US008476019B2

(12) United States Patent
Oyler et al.

(10) Patent No.: US 8,476,019 B2
(45) Date of Patent: Jul. 2, 2013

(54) ENHANCED GENE EXPRESSION IN ALGAE

(75) Inventors: George Oyler, Lincoln, NE (US); Julian Rosenberg, Naugatuck, CT (US)

(73) Assignee: Synaptic Research, LLC, Baltimore, MD (US)

( * ) Notice: Subject to any disclaimer, the term of this patent is extended or adjusted under 35 U.S.C. 154(b) by 0 days.

(21) Appl. No.: 13/504,741

(22) PCT Filed: Nov. 1, 2010

(86) PCT No.: PCT/US2010/055012
§ 371 (c)(1),
(2), (4) Date: Apr. 27, 2012

(87) PCT Pub. No.: WO2011/053935
PCT Pub. Date: May 5, 2011

(65) Prior Publication Data

US 2012/0208201 A1 Aug. 16, 2012

Related U.S. Application Data

(60) Provisional application No. 61/256,921, filed on Oct. 30, 2009.

(51) Int. Cl.
*C12Q 1/68* (2006.01)

(52) U.S. Cl.
USPC ..... 435/6.1; 435/320.1; 435/257.1; 435/69.1; 435/468

(58) Field of Classification Search
None
See application file for complete search history.

(56) References Cited

U.S. PATENT DOCUMENTS

| | | | |
|---|---|---|---|
| 2003/0145349 | A1 | 7/2003 | Odell et al. |
| 2003/0186424 | A1 | 10/2003 | Roninson et al. |
| 2006/0003416 | A1 | 1/2006 | Otte et al. |

OTHER PUBLICATIONS

Tirichine et al., The Plant Journal, vol. 66 (2011) pp. 45-57.*

Boise, Lawrence H., et al. "bcl-x, a bcl-2-Related Gene That Functions as a Dominant Regulator of Apoptotic Cell Death." Cell. Aug. 27, 1993. vol. 74. pp. 597-608. Cell Press.

Cerutti, Heriberto, et al. "Epigenetic Silencing of a Foreign Gene in Nuclear Transformants of *Chlamydomonas*." The Plant Cell. Jun. 1997. vol. 9. pp. 925-945. American Society of Plant Physiologists.

Fukuda, Hiroki, et al. "Simple histone acetylation plays a complex role in the regulation of gene expression." Briefing in Functions Genomics and Proteomics. 2006. vol. 5, No. 3. pp. 190-208. Oxford University Press.

Harris, Elizabeth H. "*Chlamydomonas* As A Model Organism." Annu. Rev. Plant Physiol. Plant Mol. Biol. 2001. vol. 52. pp. 363-406. Annual Reviews.

Joung, J. Keith, et al. "A bacterial two-hybrid selection system for studying protein-DNA and protein-protein interactions." Proc. Natnl. Acad. Sci. Jun. 20, 2000. vol. 97., No. 13. pp. 7382-7387.

Kwaks, T.H.J., et al. "Targeting of a histone acetyltransferase domain to a promoter enhances protein expression levels in mammalian cells." Journal of Biotechnology. 2002. vol. 115.pp. 35-46.

Lee, J. H., et al. "Interactions with p300 enhance transcriptional activation by the PDZ-domain coactivator Bridge-1." J. of Endocrinology . 2005. vol. 187. pp. 283-292.

Lin, Yu-Yi, et al. "A comprehensive synthetic genetic interaction network governing yeast histone acetylation and deacetylation." Genes & Developments. 2008. vol. 22. pp. 2062-2074. Cold Spring Harbor Laboratory Press.

Lumbreras, Victoria. "Efficient foreign gene expression in *Chlamydomonas reinhardtii* mediated by an endogenous intron." The Plant Journal. 1998. vol. 14, No. 4. pp. 441-447. Blackwell Science Ltd.

Nagai, Takeharu, et al. "A variant of yellow fluorescent protein with fast and efficient maturation for cell-biological applications." Nature biotechnology. Jan. 2002. vol. 20. pp. 87-90. Nature Publishing Group.

Potvin, Gabriel and Zisheng Zhang. "Strategies for high-level recombinant protein expression in transgenic microalgae: A review." Biotechnology Advances. 2010. pp. 1-9. Elsevier.

Rentahl, William and Eric J. Nestler. "Histone acetylation in drug addiction." Seminars in Cell & Development Biology. Jan. 22, 2009. vol. 20. pp. 387-394. Elsevier.

Schrode, Michael, et al. "Sequence elements within a HSP70 promoter counteract transcriptional transgene silencing in *Chlamydomonas*." The Plant Journal. 2002. vol. 31, No. 4. pp. 445-455.

Young, K. H. "Yeast Two-Hybrid: So Many Interactions, (in) So Little Time . . . " Biology of Reproduction. 1998. vol. 58. pp. 302-311.

EMBO Practical Course: Molecular Genetics of *Chlamydomonas*. Laboratory Protocols. Geneva, Sep. 18-28, 2006.

Poulsen and Kroger, A new molecular tool for transgenic diatoms. Control of mRNA and protein biosynthesis by an inducible promoter—terminator cassette, FEBS 272:3413-3423 (2005).

Cheng et al., *Agrobacterium tumefaciens* mediated transformation of marine microalgae *Schizochytrium*, Microbiological Research 167:179-186 (2012).

Kathiresan et al., *Agrobacterium*-Mediated Transformation in the Green Alga *Haematococcus pluvialis* (Chlorophyceae, Volvocales), J. Phycol. 45:642-649 (2009).

Geng et al., Stable expression of hepatitis B surface antigen gene in *Dunaliella salina* (Chlorophyta), J. Appl. Phycol. 15:451-456 (2003).

Tan et al., Establishment of a Micro-Particle Bombardment Transformation System for *Dunaliella salina*, J. Microbiol. 43(4):361-365 (2005).

Walker et al., Microalgae as bioreactors, Review, Plant Cell Rep. 24:629-641 (2005).

Walker et al., Algal Transgenics in the Genomic Era, Review, J. Phycol. 41:1077-1093 (2005).

(Continued)

*Primary Examiner* — Jim Ketter
(74) *Attorney, Agent, or Firm* — Whiteford, Taylor & Preston LLP; Joseph L. Morales

(57) ABSTRACT

The invention provides a system of enhancing the expression of transgenes in algae. Transgenes are engineered to have a binding site for certain proteins in proximity to their promoter, for example a LexA binding site. The algae is also engineered to express a nucleosome alteration protein fused to a protein with affinity to the DNA binding site acting in coordination. An example is a LexA-p300 fusion protein, where the p300 is derived from *Chlamydomonas*. The LexA binding domain guides the p300 to the binding site and the p300 loosens the nucleosome structure by acetylating histones within proximity of the transgene, thus remodeling the local chromatin structure to allow for high-level expression.

20 Claims, 4 Drawing Sheets

OTHER PUBLICATIONS

Walker et al., Characterisation of the *Dunaliella tertiolecta* RbcS genes and their promoter activity in *Chlamydomonas reinhardtii*, Plant Cell Reports 23(10-11):727-735 (2004).

Cha, Cinnamic acid, coumarin and vanillin: Alternative phenolic compounds for efficient *Agrobacterium*-mediated transformation of the unicellular green alga, *Nannochloropsis* sp, J. Microbiol. Methods 84:430-434 (2011).

Meng et al., Cloning and Characterization of β-Carotene Ketolase Gene Promoter in *Haematococcus pluvialis*, Acta Biochimica et Biophisica Sinica 37(4):270-275 (2005).

Chen et al., Conditional Production of a Functional Fish Growth Hormone in the Transgenic Line of *Nannochloropsis oculata* (Eustigmatophyceae), J. Phycol. 44:768-776 (2008).

Kunihiro et al., Development of gene expression system in a marine diatom using viral promoters of a wide variety of origin, Physiol. Plantarum 133:59-67 (2008).

Walker et al., Towards the development of a nuclear transformation system for *Dunaliella tertiolecta*, J. Appl. Phycol. 17:363-368 (2005).

Chow and Tung, Electrotrasnformation of *Chlorella vulgaris*, Plant Cell Reports 18:778-780 (1999).

Stevens and Purton, Genetic Engineering of Eukaryotic Algae: Progress and Prospects, Review, J. Phycol. 33:713-722 (1997).

Miyagawa et al., High efficiency transformation of the diatom *Phaeodactylum tricornutum* with a promoter from the diatom *Cylindrotheca fusiformis*, Phycol. Res. 57:142-146 (2009).

Kilian et al., High-efficiency homologous recombination in the oil-producing alga *Nannochloropsis* sp. PNAS 108 (52):21265-21269 (2011).

Chen et al., Highly efficient expression of rabbit neutrophil peptide-1 gene in *Chlorella ellipsoidea* cells, Curr. Genet. 39:365-370 (2001).

Weeks, Donald P., Homologous recombination in *Nannochloropsis*: a powerful tool in an industrially relevant alga, PNAS 108(52):20859-20860 (2011).

Lexun et al., Inducible EGFP expression under the control of the nitrate reductase gene promoter in transgenic *Dunaliella salina*, J. Appl. Phycol. 20:137-145 (2008).

Wang et al., Rapid isolation and functional analysis of promoter sequences of the nitrate reductase gene from *Chlorella ellipsoidea*, J. Appl. Phycol. 16:11-16 (2004).

Apt et al., Stable nuclear transformation of the diatom *Phaeodactylum tricornutum*, Mol. Gen. Genet. 252:572-579 (1996).

Miyagawa et al., Stable nuclear transformation of the diatom *Chaetoceros* sp., 59:113-119 (2011).

El-Sheekh, M.M., Stable transformation of the intact cells of *Chlorella kessleri* with high velocity microprojectiles, Biol. Plantarum 42(2):209-216 (1999).

Fisher et al., Targeting and Covalent Modification of Cell Wall and Membrane Proteins Heterologously Expressed in the Diatom *Cylindrotheca fusiformis* (Bacillariophyceae), J. Phycol. 35:113-120 (1999).

Mitra and Higgins, The *Chlorella* virus adenine methyltransferase gene promoter is a strong promoter in plants, Plant Mol. Biol. 26:85-93 (1994).

Poulsen et al.,Molecular Genetic Manipulation of the Diatom *Thalassiosira pseudonana* (Bacillariophyceae), J. Phycol. 42:1059-1065 (2006).

Thiel and Poo, Transformation of a Filamentous Cyanobacteriumby Electroporation, J. Bacteriol. 171(10):5743-5746 (1989).

Zaslayskaia et al., Transformation of the Diatom *Phaeodactylum tricornutum* (Bacillariophyceae) with a variety of selectable marker and reporter genes, J. Phycol. 36:379-386 (2000).

Steinbrenner and Sandmann, Transformation of the Green Alga *Haematococcus pluvialis* with a Phytoene Desaturase for Accelerated Astaxanthin Biosynthesis, Appl. and Env. Microbiol. 72(12):7477-7484 (2006).

Teng et al., Transient expression of IacZ in bombarded unicellular green alga *Haematococcus pluvialis*, J. Appl. Phycol. 14:495-500 (2002).

Cadoret et al., Microalgae, Functional Genomics and Biotechnology, Advances in Botanical Research 64:285-342 (2012).

Coll, J.M., Review. Methodologies for transferring DNA into eukaryotic microalgae, Spanish J. Agric. Res. 4(4):316-330 (2006).

Franklin, Scott E., et al. "Prospects for molecular farming in the green *alga Chlamydomonas reinhardtii*." Current Opinion in Plant Biology. vol. 7. Apr. 1, 2004 pp. 159-165.

Leon-Banares, R., et al. "Transgenic microalgae as green cell-factories." Trends in Biotechnology. vol. 22, No. 1. Jan. 1, 2004. pp. 45-52.

Specht, Elizabeth, et al. "Micro-algae come of age as a platform for recombinant protein production." Biotechnology Letters. vol. 32, No. 10. Jun. 17, 2010.

Waterborg, J.H. "Dynamics of Histone Acetylation in *Chlamydomonas reinhardtii*." Journal of Biological Chemistry. vol. 273, No. 42. Oct. 16, 1998.

Supplementary European Search Report issued in corresponding European Patent Application No. EP 10 82 7622 on Mar. 15, 2013.

* cited by examiner

ENHANCED GENE EXPRESSION IN ALGAE

CROSS REFERENCE TO RELATED APPLICATIONS

This application claims the priority benefit under 35 U.S.C. §119(e) of U.S. Provisional Application Ser. No. 61/256,921, entitled "ENHANCED GENE EXPRESSION IN ALGAE" filed Oct. 30, 2009, which is incorporated herein by reference in its entirety.

BACKGROUND OF THE INVENTION

1. Field of the Invention

This invention relates to the field of molecular biology and in particular to the expression of transgenes in algae.

2. Description of the Background

Transgenes are foreign DNA sequences introduced into genomes, in the case of eukaryotic cells within the chromosomes. These genes are usually transcribed as any other gene of the host. Transcription is generally controlled by the chromatin structure that packs the chromosome's DNA into tight bundles in eukaryotic organisms called nucleosomes. As the chromatin structure around a specific gene relaxes, the DNA of the particular gene becomes accessible to the transcription machinery of the cell. Staining indicates that actively transcribed genes in eukaryotes are more loosely incorporated in nucleosomes and more prevalent in euchromatin. In some instances, transgenes are incorporated into the host's chromosome but fail to be expressed due to unfavorable chromatin structures. This phenomenon is called "gene silencing." The ability to control how tightly a nucleosome is packed can help enhance the expression of transgenes in host cells. In mammalian cells, it has been proposed that coupling transgene expression with increased availability of a histone "tail" modifying gene, p300 (also known as a histone acetyl transferase, or "HAT"; in the family of CREB binding proteins, or "CBP"), can increase the expression level, presumably because the acetyl transferase activity causes a looser histone-DNA association and allows transcription factors access to the genes. T. H. J. Kwaks et al., J. Biotechnology, 115:35-46 (2005).

Microalgae encompass a broad range of organisms, mostly unicellular aquatic organisms. The unicellular eukaryotic microalgae (including green algae, diatoms, and brown algae) are photosynthetic and have a nucleus, mitochondria and chloroplasts. The chromatin structure in algae is distinct from other eukaryotes. The chromatin in algae stains heavily, indicating a more compact nucleosome structure and tight association of the DNA to the histones. These differences in chromatin structure of microalgae, particularly in green algae, suggest distinct mechanism of histone chromatin regulation of gene expression.

These differences in eukaryotic microalgae chromatin structure may be the factor behind the observation that stable nuclear transgene expression in microalgae is difficult and transient due to chromatin mediated gene silencing. H. Cerutti, A. M. J., N. W. Gillham, J. E. Boynton, *Epigenetic silencing of a foreign gene in nuclear transformants of Chlamydomonas*, The Plant Cell 9:925-945 (1997). When genetic constructs comprising a mammalian derived anti-apoptotic gene and a fluorescent reporter gene were previously introduced by the present inventors in algae, the expression levels were low and no expression of the fluorescence gene was detected, thus confirming that transgenes are difficult to express in algae.

Algae are considered an important source of healthy nutrients for human consumption and are important as biomass and biofuels. Genetic engineering and stable (over multiple generations) expression of transgenes would open new horizons and greatly enhance the value and desirability to beneficially culture algae. However, as noted above, stable and sufficiently high level of gene expression has been difficult to achieve. A method to improve transgene expression in algae and make that expression stable would be very useful. Such an approach would need to account for the uniquely robust histone mediated gene silencing of microalgae including green algae.

SUMMARY OF THE INVENTION

In accordance to one embodiment, the invention provides a system for enhanced gene expression in algae, the system comprising:

an algae compatible transcriptional promoter functionally upstream of a coding sequence for a gene expression enhancer (GEE) fusion protein, wherein the fusion protein comprises an algae derived p300 functionally fused to the DNA binding protein, wherein at least the portion of the coding sequence of the DNA binding protein domain is codon optimized for improved expression in an algae;

at least one transgene functionally downstream of an algae compatible transcriptional promoter; and at least one DNA region that is a binding site for the DNA binding protein, in vicinity of at least one of said transcriptional promoters;

wherein said system resides in an algae.

In a preferred embodiment, the DNA binding protein is LexA DNA Binding domain. In another preferred embodiment, the p300 part of the GEE fusion protein is from *Chlamydomonas reinhardtii*. In a more preferred embodiment, only a HAT domain of the p300 protein is part of the GEE fusion protein. The p300 or only the HAT domain of p300 may be derived from homologs of other microalgae including green algae in addition to *Chlamydomonas reinhardtii.*

In accordance to another embodiment, the transgene is codon modified for improved expression in algae. In a preferred embodiment, the transgene or gene of interest (GOI) is a fluorescence-Bcl-$x_L$ fusion gene. The fusion protein may include a fluorescence-Bcl-$x_L$ construct (e.g. YFP-Bcl-$x_L$ fusion or a Venus-Bcl-$x_L$ fusion). In another preferred embodiment, the transgene is the YFP/Venus gene, not necessarily part of a fusion protein. Venus is an enhanced yellow fluorescent protein (YFP) that is stable over a wide range of pH, folds quickly, and emits at 30-fold the intensity of conventional YFP. Nagai T., Ibata K., Park E. S., Kubota M., Mikoshiba K. and Miyawaki A. (2002). A variant of yellow fluorescent protein with fast and efficient maturation for cell-biological applications. *Nature Biotechnol,* 20, 87-90.

In accordance to another embodiment, the system further comprises at least one selective marker such as an antibiotic resistance marker. In a preferred embodiment, the GEE fusion protein and the at least one transgene are introduced into the system on one vector and structurally arranged to be expressed from one bidirectional promoter region and comprising DNA binding sites in the vicinity of both promoters. In a more preferred embodiment, the GEE fusion protein and the transgene are introduced in the system on separate vectors, each comprising a selective marker and the selective markers are not the same. When separate vectors, both the GEE vector and the vector for the gene of interest (GOI) will contain selective markers. When the GEE is introduced on a separate vector from the vector for the GOI, the GEE vector may be used to generate a stable algae cell line that will serve as the recipient for the second vector expressing the GOI. This stable GEE algae cell line will function to enhance the expression of the second vector containing the GOI.

In accordance to yet another embodiment, the algae compatible transcriptional promoters are hsp70, rbcS, nitA, actin, tubA2 or a combination thereof.

In accordance to another yet embodiment, the GEE fusion protein comprises a DNA binding domain functionally fused to an algae derived p300 homologue having at least 80% identity over the HAT region to the p300 from *Chlamydomonas reinhardtii*. Preferably, the GEE fusion protein comprises a DNA binding domain functionally fused to the HAT domain of the HAT region to the p300 from *Chlamydomonas reinhardtii*. It is noteworthy that the p300 from mammalian species is much larger in size and is much less that 50% similar to *Chlamydomonas reinhardtii* p300.

The invention also provides a method of expressing a gene in algae at higher levels, comprising:

transforming algae with at least one vector comprising:

an algae compatible transcriptional promoter functionally upstream of a coding sequence for a gene expression enhancer (GEE) fusion protein, wherein the fusion protein comprises an algae derived p300 functionally fused to the DNA binding protein, wherein at least the portion of the coding sequence of the DNA binding protein domain is codon optimized for improved expression in an algae;

at least one transgene functionally downstream of an algae compatible transcriptional promoter; and at least one DNA region that is a binding site for the DNA binding protein, in vicinity of at least one of said transcriptional promoters;

selecting a transformed algae cell; and detecting the expression of said GEE gene and/or said transgene in algae.

In a preferred embodiment, the DNA Binding protein is the LexA binding domain, and more preferably the p300 is from *Chlamydomonas reinhardtii*. More preferably yet, the GEE fusion protein comprises the LexA binding domain functionally fused with the HAT domain of the p300 protein from *Chlamydomonas reinhardtii*.

In accordance to another embodiment, the transgene is a YFP-Bcl-$x_L$ fusion protein or a Venus-Bcl-$x_L$ fusion protein.

In accordance to yet another embodiment, the GEE fusion protein and said transgene are transformed in algae on separate vectors, first selecting a vector stably expressing the GEE fusion protein and then transforming the selected algae with the vector comprising the transgene.

BRIEF DESCRIPTION OF THE DRAWINGS

FIG. 2A is a vector expressing a LexA-p300 fusion protein. FIG. 2B illustrates a vector expressing another gene which is advantageously introduced in algae ("gene of interest or "GOI"). In accordance to this embodiment, each of the LexA-p300 fusion and the GOI have, at or near their 5'-ends, LexA binding site(s).

DETAILED DESCRIPTION

Figure 1:
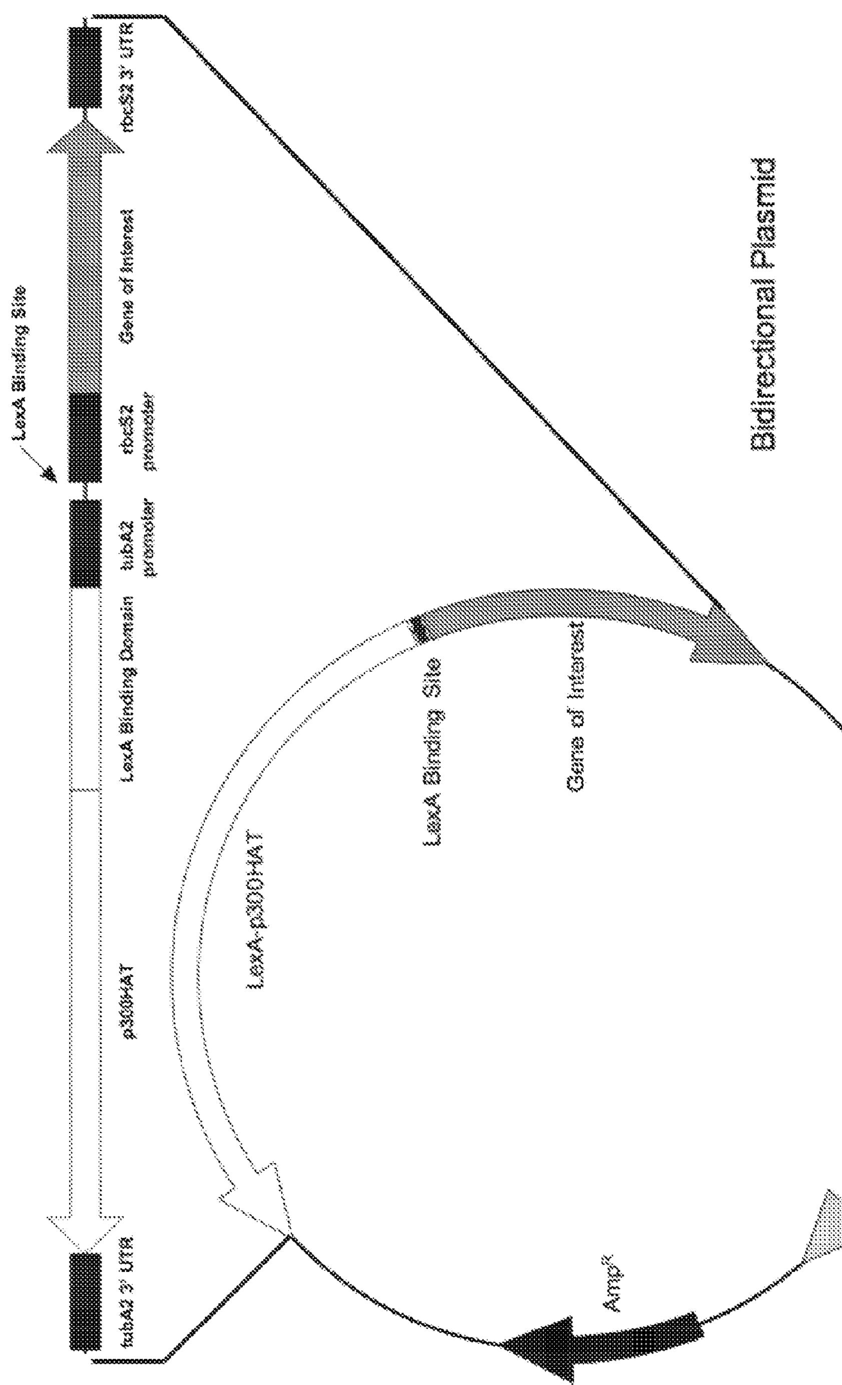
FIG. 1 illustrates the features of a vector in accordance to one embodiment of the present invention. The direction of transcription is indicated by arrows. The figure indicates certain structural components, as discussed herein elsewhere. The linear drawing provides further details of the respective region of the vector: a fused LexA-p300 protein coding region and a coding region of a GOI. In this embodiment, these two coding regions are transcribed in opposite directions (thus the "bidirectional" nomenclature). These two coding regions are separated by a locus comprising LexA binding sites.

Expression of transgenes in the algae is difficult. H. Cerutti, A. M. J. et al., The Plant Cell 9:925-945 (1997). Likewise, when the present inventors transformed a microalgae with a construct expressing a yellow florescence protein ("YFP") fused to a cancer suppressing Bcl-$x_L$ gene (the transcription driven by the rubisco promoter (rcbS2) and relying on a heat shock translational enhancer (HSP70)), the transformed microalgae failed to produce fluorescence. However, transformants which survived marginally longer and were morphological affected (the result of limited expression of the Bcl-$x_L$ gene) were observed. It is expected that that gene silencing contributed to the poor expression of the transgenes in algae.

The present invention provides an effective method to increase transgene expression in algae, preferably a green algae, more preferably a microalgae. A preferred algae of the invention is an unicellular, photosynthetic algae. A yet more preferred algae is the microalgae. The GOI transgene expressed in the algae in accordance to the invention is expressed to a higher level. The expression is increased by at least 50%, preferably about two to at least five fold, relative to the expression of the same transgene engineered in the algae without the benefit of the present invention. In respect of fluorescence transgenes, the expression is increased sufficiently to allow monitoring the fluorescence signal. More preferably, the fluorescence signal is monitored in *Chlamydomonas.*

The transgene is introduced in algae. In accordance with an embodiment of the present invention, the transgene is placed on a vector. The vector is a nucleic acid structure used to introduce a cassette containing a DNA sequence into an algae chromosome. The vector is introduced in the nucleus of a host algae cell and the transgene is transcribed/translated in the algae. Methods of transformation of algae are well known to artisans skilled in the art. For example, a vector construct may be introduced via electroporation, via plasmid conjugation, and via particle bombardment. The transformed algae arc recovered on a solid nutrient media or in liquid media. Elizabeth H Harris, *Chlamydomonas As A Model Organism*, Annual Review of Plant Physiology and Plant Molecular Biology 52:363-406 (2001) and EMBO Practical Course: Molecular Genetics of *Chlamydomonas*, Laboratory protocols. Geneva, Sep. 18-28, 2006.

A preferred vector of the invention is a plasmid capable of integrating the DNA sequence of interest into a chromosome of the algae. There are a large numbers of vectors known and characterized. A preferred vector of the invention is pSP124. Lumbreras et al., Efficient foreign gene expression in *Chlamydomonas reinhardtii* mediated by an endogenous introns, The Plant Journal 14(4):441-447 (1998).

Methods of engineering vectors are well known in the art. The vector backbone may include genes encoding transformation markers, to indicate transformation of the host cell with the vector. A transformation marker may be a selective marker gene used to select cells in which the vector is present from normal cells without the vector. Selective markers are well known to artisans skilled in the art. Commonly used selective markers include genes that confer resistance to specific antibiotics such as bleomycin. Only cells containing the vector grow in media containing the antibiotic. Other vector backbones may also include marker genes that merely indicate which cells were transformed. When such markers are used, cells with and without the vector will grow but the cells containing the vector can be distinguished from those not having the vector because they display a specific characteristic conferred by the vector, e.g., color. A commonly used transformation marker gene is the yellow or green fluorescence gene. Cells containing a vector with such a gene will be yellow or green. Other common transformation markers include various luciferase genes. Cells containing the luciferase genes emit light.

Any effective combination of gene expression regulatory features compatible with expression of genes in the algae nucleus can be incorporated in the vector. The plasmid may include different types of promoters, for example constitutive promoters or inducible promoters. Preferred transcriptional promoters in accordance to the invention include the hsp70 ("heat shock protein" promoter), rbcS ("rubisco small subunit" promoter) and tubA2 ("actin" promoter). The vector employs suitable translational enhancer elements, generally referred to as 5'untranslated regions or "5'UTR." Preferred enhancers in accordance to the invention are the tubA2 intron 1, the HSP70 enhancer, and the rcbS2 intron 1. The vector of the invention includes also effective translational terminators, 3'UTR. Examples of preferred 3'-UTR sequences include the tubA2, HSP70, and rcbS2 3'UTR. Other effective promoters, transcription enhancers and terminators may, in particular combinations, may produce satisfactorily high and stable expression.

Figure 2A:
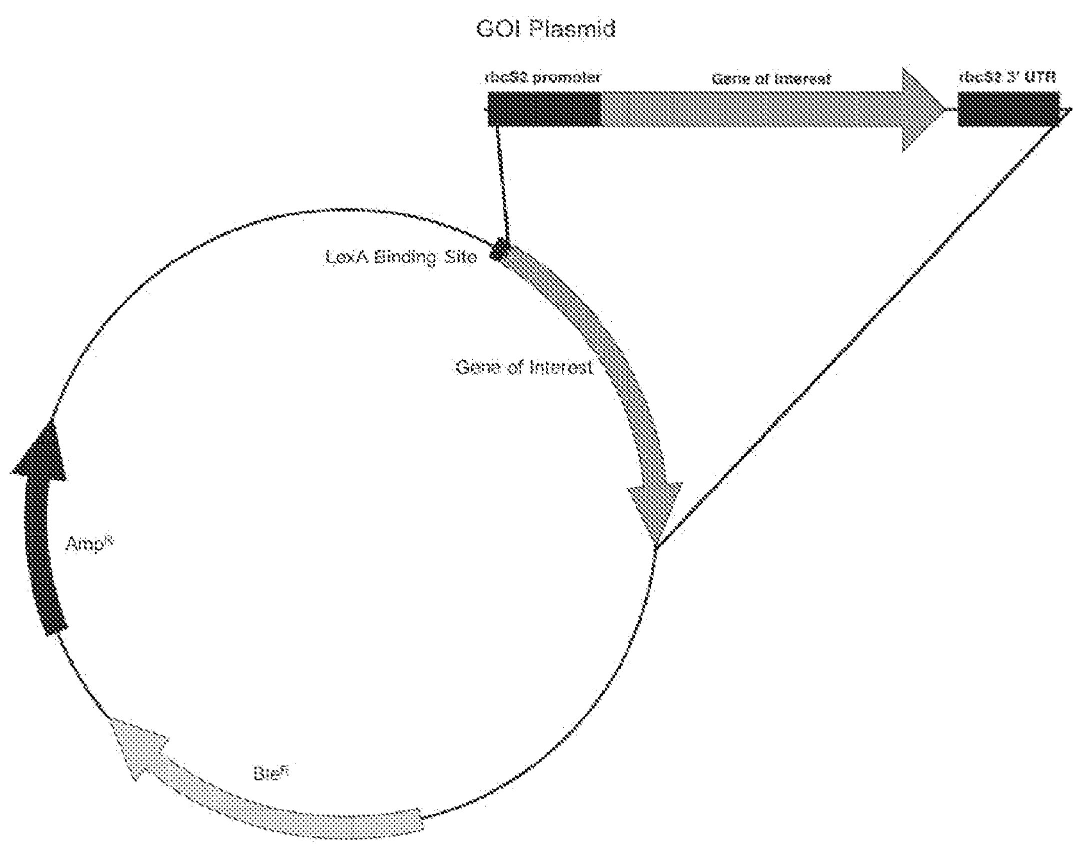
FIGS. 2A and 2B illustrate another embodiment of the invention.

Some of these options are illustrated in FIGS. 1 and 2. The features selected to be exemplified in FIGS. 1 and 2 include the promoter and 3' UTR regions of the Chlamy genes: tubA2 encoding actin (Tubulin); rbcS2 encoding the rubisco small subunit; or nitA encoding nitrate reductase. Furthermore, the hsp70A/rbcS2 tandem promoter is a preferred driver of transgene expression. Schroda M., Beck C. F. and Vallon A., Sequence elements within an hsp70 promoter counteract transcriptional transgene silencing in *Chlamydomonas*. Plant J. 31:445-455 (2002). This chimeric promoter contains the enhancer region of the nucleo-cytoplasmic-localized 70 kD heat shock protein gene (NCBI GenBank ID: M76725; by 572-833) and the promoter from the nuclear rubisco small subunit gene (NBCI GenBank ID: X04472; by 934-1142). Additionally, the first intron (bp 1307-1451) and 3'-untranslated region (bp 2401-2632) of the rbcS2 gene may be included to further promote stable transgene expression.

In accordance with an embodiment of the present invention, one or more vectors are used to introduce a cassette that contains a gene of interest ("GOI") and a gene silencing inhibitor into the nucleus DNA of algae, e.g., a Chlamy nucleus. The GOI can be any gene desirably expressed in algae. Viable genes of interest include genes involved in controlling algae's metabolic pathways. For example, in one embodiment of the present invention the Bcl-$x_L$ gene can be inserted and expressed in the algae's nucleus. Bcl-$x_L$ is an abbreviation for B-cell lymphoma extra-large; it is known to be an inhibitor of apoptosis (programmed cell death). Boise L. H. et al., *Bcl-x, a bcl-2-related Gene that Functions as a Dominant Regulator of Apoptotic Cell Death*, Cell 74:597-608 (1993). In another embodiment genes affecting lipid or isoprenoid production pathways are desirably introduced. Due to Bcl-$x_L$'s ability to inhibit apoptosis, its expression allows algae cells to live longer. A longer lifespan for microalgae enables the use of microalgae in various industrial applications such as photobioreactors.

A gene silencing inhibitor is also introduced into the algae. A gene silencing inhibitor is a peptide that induces relaxation of nucleosomes in the algae's nucleus. Gene silencing inhibitors include histone acetyl transferases (HATs) and other peptides that modify elements of the nucleosome, causing the chromatin structure to relax and to allow transcription factors to access the gene of interest. HAT proteins and the HAT domains of p300 and of other HAT proteins are known to cause histone acetylation and can be utilized in the invention. In accordance to the invention the domain responsible for the acetylation activity or the whole protein is deployed. See Fukuda H, et al., Brief Funct. Genomic Proteomic, 5(3):190-208 (2006); Renthal W. and Nestler E. J., Semin Cell Dev Biol. 20(4):387-94 (Epub 2009); and Lin Y. Y. et al., Genes Dev., 22(15):2062-74 (2008).

One preferred embodiment of the present invention utilizes a p300 protein as a gene silencing inhibitor. More preferably, a Chlamy derived p300 protein is utilized. In a yet more preferred embodiment, the Chlamy p300 protein is the homologue detailed in FIG. 3. In a further more preferred embodiment, only the HAT domain of the Chlamy p300 gene is utilized. See FIG. 3 and relevant portion of SEQ ID NO 4.

Figure 3:
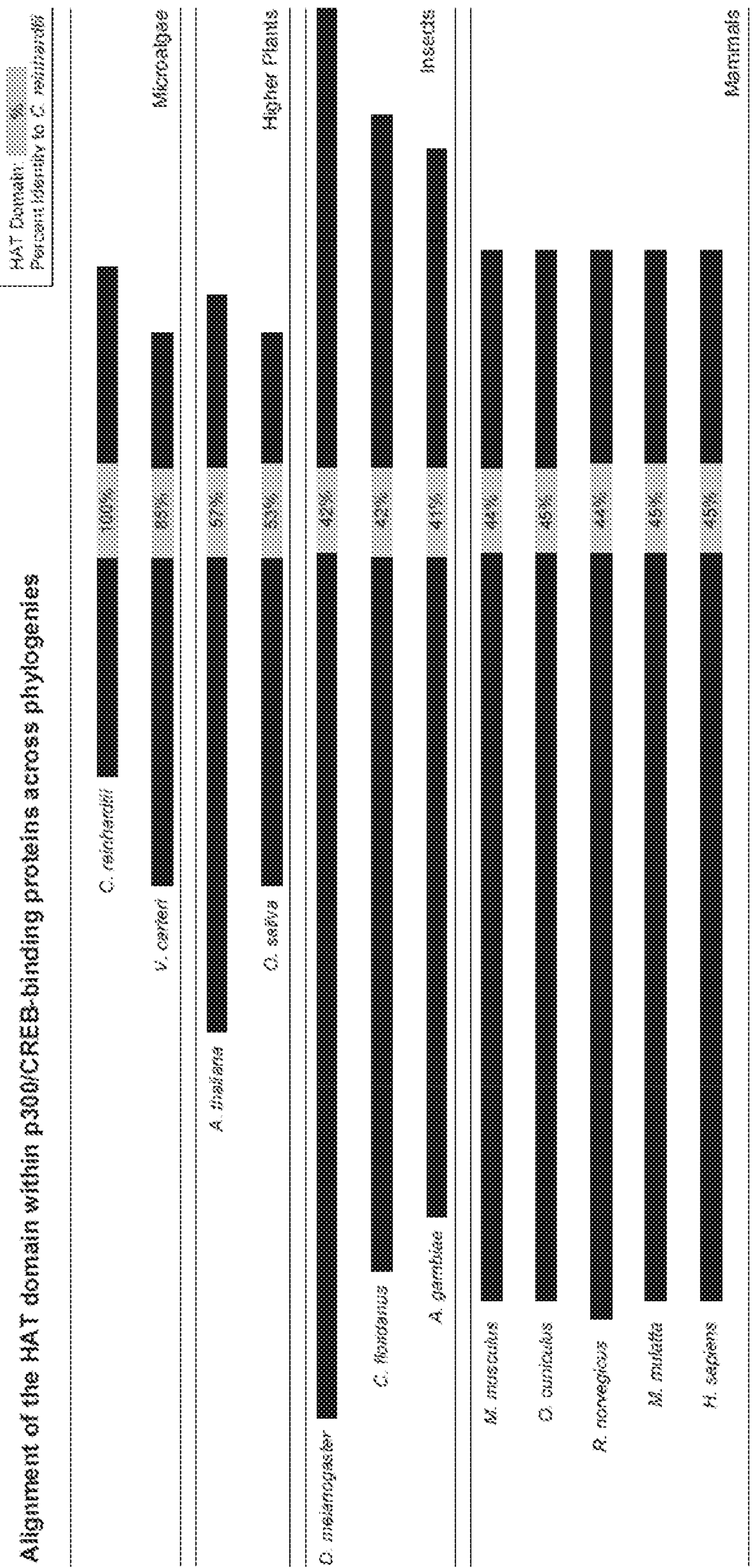
FIG. 3 compares the putative p300 protein from algae (*Chlamydomonas reinhardtii* ("Chlamy") with known p300 proteins from the indicated phylogenetically representative species. The lighter colored section of each bar represents the histone acetylase (HAT) domain. The HAT domains are aligned for visualization purposes. These lighter bars include numbers that are indicative of the percent identity of the HAT domain of each protein proteins within each panel, with the indicated percentages of identity of each HAT protein to the p300 HAT domain of the p300 protein from Chlamy. The figure is drawn to scale, both in respect to the overall size of the p300 proteins and the location of the HAT domain within the protein.

FIG. 3 shows an alignment comparison of the Chlamy p300 with phylogenetically distinct other p300 homologues. The lighter colored section of each bar represents the histone acetylase (HAT) domain. The HAT domains are aligned for visualization purposes. These lighter bars include numbers that are indicative of the percent identity of the HAT domain of each protein proteins with the indicated percentages of identity of each HAT protein to the p300 HAT domain of the p300 protein from Chlamy. FIG. 3 is drawn to scale, both in respect to the overall size of the p300 proteins and the location of the HAT domain within the protein.

Table 1, exemplifies the highly conserved nature of the p300 proteins and particularly conserved nature of the HAT domains.

TABLE 1

Comparison of HAT domain identity within each phylogenetic clade. The bolded organism at the top of each column is the representative species to which all other percent identities are based.

| ***C. reinhardtii* - 100%** | ***A. thaliana* - 100%** | ***D. melanogaster* - 100%** | ***H. sapiens* -100%** |
|---|---|---|---|
| *V. carteri* - 85% | *G. max* - 91% | *A. gambiae* - 92% | *M. mulatta* - 100% |
| | *O. sativa* - 91% | | *O. cuniculus* - 100% |
| | *S. bicolor* - 90% | *C. floridanus* - 89% | *R. norvegicus* - 99% |
| | *P. trichocarpa* - 88% | | *M. musculus* - 99% |
| Microalgae | Higher Plants | Insects | Mammals |

Indeed, the percent identity between plant and mammalian p300 homologues is also very high, typically at least about 80%. See US Patent Publication US2003/0145349. However, the homology of the Chlamy p300 homologue to other organisms is lower. Likewise, the p300 full protein of *Chlamydomonas reinhardtii* is 11.5% identical and further 9.9% similar to the mouse p300 protein; 9.1% identical and a further 4.7% similar to the *Drosophila* p300 protein; and 23.6% identical and a further 9.9% similar to the *Arabidopsis* p300 protein. The Chlamy derived protein has N-terminal or C-terminal regions which are shorter and dissimilar in their location visa-vie the HAT domain to these of the mammalian or plant p300 proteins. See FIG. 3. This is suggestive of proteins with overall distinct functions and phylogeny.

The various proteins p300 homologues in FIG. 1 and described herein elsewhere are:

*C. reinhardtii* p300/HAT Protein ID: 159467703 from NCBI Database.
*V. carteri* p300/CBP Protein ID: 300256266 from NCBI Database.
*S. bicolor* putative p300 Protein ID: C5XTZ4 from Universal Protein Resource.
*P. trichocarpa* GenBank ID: POPTR_007s15090 from Joint Genome Institute Database.
*G. max* Protein ID: PF02135 from Joint Genome Institute Database.
*A. thaliana* HAC1/p300/CBP GenBank ID: NM_106550.3 from NCBI Database.
*O. sativa* p300/CBP Protein ID: 108792657 from NCBI Database.
*D. melanogaster* CBP/HAT Genbank ID: NM_079903.2 from NCBI Database.
*A. gambiae* HAT Protein ID: 158289391 from NCBI Database.
*C. floridanus* CBP Protein ID: 307172990 from NCBI Database.
*M. musculus* E1A/BP/p300 GenBank ID: NM_177821.6 from NCBI Database.
*O. cuniculus* p300 Protein ID: 291410334 from NCBI Database.
*R. norvegicus* p300 Protein ID: XP_576312.3 from NCBI Database.
*M. mulatta* p300 HAT Protein ID: XP_001102844.1 from NCBI Database.
*H. sapiens* p300 Protein ID: NP_001420.2 from NCBI Database.

In another preferred embodiment of the present invention, the gene silencing inhibitor is functionally tethered or, preferably, fused to a DNA binding protein or domain thereof (the tethered/fused protein or its/their gene hereinafter are referred to as the gene expression enhancer unit, or "GEE"). The DNA binding protein or domain binds to a particular DNA sequence (Binding Site or "BS"), bringing the gene silencing inhibitor to its histone target at a location in the vicinity of the BS and thereby inducing relaxation of the nucleosome at that genetic location. As the nucleosome relaxes, the nearby DNA sequence is exposed to transcription factors and is more actively transcribed.

In accordance to a preferred embodiment, the invention requires the expression in an algae protein that binds specific DNA sequences, which sequences can be engineered upstream of any GOI for expression in algae. The DNA binding protein/domain can be any protein having known DNA binding sites can be used. Examples of proteins targeting specific DNA motifs applicable to this invention include the Gal4 protein and Early Growth Response Protein 1. DNA binding site motifs for these proteins are known. Likewise, the binding domains of these as well as the LexA protein are known and are preferentially used, instead of the full-length protein. See for example Young, K., Biol. Reprod., 58:302-311 (1998) and Joung, J. et al., Proc. Natnl. Acad. Sci., 97:7382-7 (2000). The DNA binding site (BS) for Gal4 is 5'-CGGAGGACAGTCCTCCG-3' (SEQ ID NO 10).

LexA is a preferred example of a DNA binding protein. LexA is a gene of bacterial origin. LexA proteins or genes are not known in algae. Thus, it is unlikely that the Chlamy genome will contain the DNA binding sequence of LexA. The function of LexA in the context of the invention is to bind a particular DNA sequence (binding site, "BS"). LexA binding sites are found upstream promoters in a number of microorganisms. A consensus BS sequence for LexA is CTGTATATATATACAG. SEQ ID NO 9. The binding domain of the LexA protein is known and, for the purpose of the invention, it is preferred to employ only the binding domain. Protein ID: 2293118 from NCBI Database:

```
                                         (SEQ ID NO 11)
MKALTARQQEVFDLIRDHISQTGMPPTRAEIAQRLGFRSPNAAEEHLKA

LARKGVIEIVSGASRGIRLLQEEEEGLPLVGRVAAGEPLLAQQHIEGHY

QVDPSLFKPNADFLLRVSGMSMKDIGIMDGDLLAVHKTQDVRNGQVVVA

RIDDEVTVKRLKKQGNKVELLPENSEFKPIVVDLRQQSFTIEGLAVGVI

RNGDWLEFPGIRRPWRPLESTCSQANSGRISYDL.
```

As noted above, the DNA binding protein or domain thereof, preferably the LexA domain, is constructed to translate in a protein allowing the DNA binding domain and a nucleosome relaxation protein to act in concert. Any nucleosome relaxation protein might be used. Preferably, as noted above, a Chlamy p300 domain is used.

Without being limited to a single mechanism of action, it is proposed that one partner binds to the DNA, the other acetylates nearby histones, thereby creating a looser association between the DNA and the histones at that site. Therefore any method to render the DNA binding domain and the acetylase domain spatially close to each other is preferred. A fused protein is more preferred. The order of the two units (N-terminal proximity) within the fusion protein is not critical. However, in the p300-LexA binding domain example, it is preferred that LexA binding domain is at the N-terminal end of the fusion. "Functional" fusion proteins are designed. By way of example, certain linker regions are introduced to allow flexibility, orientation or simply "dead" protein sequence corresponding to strategically placed genetic engineering features such as primers and restriction enzyme sites.

Preferably, the GEE can be a p300 peptide homolog and the DNA binding domain can be LexA binding domain, creating a p300-LexA binding domain fusion protein and its gene construct. Preferably, that fusion is an algae p300-LexA binding domain fusion. More preferably, the fusion is the Chlamy p300-LexA fusion. Alternatively, the fusion comprises select domains of the Chlamy p300-LexA proteins. See SEQ ID NO 4. Yet more preferably, the fusion, at the nucleic acid level, comprises a LexA sequence modified in its codon usage for higher yield when expressed in algae. Preferably, the whole of the GEE fusion protein gene was designed for preferred codon usage in algae, even if part of the gene (p300) is an algae derived gene, as provided by SEQ ID NO 1 and SEQ ID NO 3. Indeed, the transgene (GOI) and other genes in the system preferably arc codon optimized based on codon frequency in algae.

It should be noted that other algae p300 homologues or their acetylasehistone acetyltransferase (HAT) domains may be preferentially used in the invention. However, these preferred homologues must be at least about 60% identical to the Chlamy p300, preferably at least about 70% identical, at least about 80% identical, at least about 85% identical, at least about 90% identical or more. A p300 homologue from *V. carteri* (algae) was recently identified. It has about 85% identity to the Chlamy p300, over the HAT domains.

The LexA-p300 fusion DNA (SEQ ID 1) is the nucleotide sequence encoding a fusion protein (exemplary GEE) comprising the LexA binding domain and the full length Chlamy p300 sequence, all of the fusion designed to reflect preferred codon usage in algae. It was adapted to the nuclear codon usage of *C. reinhardtii* according to the table provided by the Kazusa Codon Usage Database (Species ID: 3055), using Gene Designer software from DNA 20. The sequence up to nucleotide 690 is that of the LexA DNA binding domain and the fell length *C. reinhardtii* p300 sequence begins at nucleotide 700. A 3-amino acid peptide linker (GVL) connects LexA binding domain and p300, which represents the DNA restriction site PpuMI (9 bp). The LexA gene sequence is codon-optimized for *C. reinhardtii* nuclear expression using AA sequence from Protein ID: 2293118 from NCBI Database:

```
                                                       SEQ ID NO 1
   1  ATGAAGGCTCTGACCGCTCGCCAGCAGGAGGTGTTTGATCTGATTCGGGA

  51  CCATATCAGCCAAACGGGCATGCCCCCTACGCGCGCGGAGATCGCGCAAC

 101  GGCTGGGCTTCCGCTCCCCGAACGCGGCTGAGGAGCACCTGAAGGCGCTG

 151  GCGCGCAAGGGTGTGATTGAGATCGTCTCCGGCGCGTCGCGGGGCATTCG

 201  GCTGCTGCAGGAGGAGGAGGAGGGTCTGCCTCTGGTGGGGCGGGTGGCTG

 251  CGGGCGAGCCCCTGCTGGCCCAGCAGCACATTGAGGGCCACTACCAAGTG

 301  GACCCGTCCCTCTTCAAGCCGAACGCCGATTTCCTGCTGCGCGTCAGCGG

 351  TATGAGCATGAAGGACATCGGCATCATGGACGGTGACCTGCTGGCCGTGC

 401  ATAAGACGCAGGACGTGCGCAACGGCCAAGTGGTCGTCGCCCGCATCGAT

 451  GACGAGGTGACCGTGAAGCGCCTGAAGAAGCAGGGGAACAAGGTCGAGCT

 501  GCTGCCCGAGAACAGCGAGTTCAAGCCCATCGTGGTGGATCTGCGCCAGC

 551  AATCCTTCACCATCGAGGGCCTGGCGGTGGGCGTGATCCGCAACGGCGAC

 601  TGGCTGGAGTTCCCGGGCATCCGCCGCCCGTGGCGCCCTCTGGAGTCCAC

 651  GTGCTCGCAGGCCAACTCCGGCCGCATTAGCTACGACCTGGGGGTCCTTA

 701  TGGTGCCGATGGGCGCGCCCGCTATGCCCATGGGCAACAACGGCTCGCCC

 751  ATGCTGAACGGCATGGGTATGTTCAACGCCCCGCAGCAGACCGTGCCCAA

 801  CGGCGGGCCGGGTGGCGTGAACCCCATGGGCCAGGTGCCGGCGATGCCTG

 851  CGCCGATCCCCAACGGCGGTCTGCCCGGTATGAACGCTGCCGGCGGTGCC

 901  GACGATCCTGCGAAGCAGCGGGAGCAATCGATCCAGAAGCAGCAGCGCTG

 951  GCTGCTGTTCCTGCGGCACTGCGCGAAGTGCCGGGCTCCCGGCGAGGACT

1001  GCCAGCTGAAGTCCCAGTGCAAGTTCGGCAAGCAGCTGTGGCAGCACATC

1051  CTGTCGTGCCAAAACCCGGCCTGCGAGTACCCGCGCTGCACCAACTCCAA

1101  GGATCTGCTCAAGCACCACCAGAAGTGCCAGGAGCAGACCTGCCCCGTGT

1151  GCATGCCGGTGAAGGACTACGTGAAGAAGACGCGCCAGGCGACCCAACAG

1201  CAGCAACAAATGCAGCAACAACAGCAAATCCAGCAACAGCAACAACAACA

1251  AATGCAACAGCAACAGATGCAACAGCAGCAGCTCCAGCAGCAGCAGATGC

1301  AACAACAACAGCAGATGCAGCAGCAGCAACAGCCCGGCGTGGGCGCCAAC

1351  TTCATGCCCACCCCGCCCATGATGCCGAACGGCATGTTCCCTCAACAGCA

1401  GCCCCAGCAGGCGATGCGCCTGAACGCCAACGGCCTCGGCGGCCAGAAGC

1451  GCCCCCACGAGATGATGGGTATGTCCAGCGGCGGCATGGACGGTATGAAC

1501  CAGATGGTGCCCGTCGGCGGCGGCGGCATGGGCATGTCGATGCCGATGGG

1551  TATGAACAACCCCATGCAGGGCGGTATGCCCCTGCAGCCTCCGCCCCAGG
```

-continued

```
1601 TGCAGGCTCCCGGTCAGGGCCCCATGATGAGCGCCCCTCAGCAGCAACAG
1651 CAGCAACCGGCCCCTAAGCGGGCGAAGACCGACGATGTGCTGCGCCAGAA
1701 CACGGGCACCAGCCTCCTGGAGACGTTCGACGCCAAGCAGATCCGCGTGC
1751 ACGTGGACCTGATCCGCGCTGCCGCGGTGACCCAGAAGGCCCAGCAGCCT
1801 CCCCCGGCTAACCCCGACGACGCGTGCAAGGTCTGCGCGCTGACGAAGCT
1851 GTCGTTCGAGCCCCCGGTGATTTACTGCTCGAGCTGCGGCCTGCGCATCA
1901 AGCGCGGCCAGATCTTCTACAGCACGCCTCCGGACCACGGCAACGACCTG
1951 AAGGGTTACTTCTGCCACCAGTGCTTCACCGACCAGAAGGGCGAGCGCAT
2001 CCTGGIGGAGGGCGTCTCGATCAAGAAGAGCGACCTGGTGAAGCGCAAGA
2051 ACGATGAGGAGATCGAGGAGGGGTGGGTGCAGTGCGACCACTGCGAGGGC
2101 TGGGTGCACCAGATTTGCGGCATGTTCAACAAGGGCCGGAACAACACGGA
2151 CGTCCACTACCTGTGCCCTGACTGCCTGGCCGTGGGCTACGAGCGCGGCC
2201 AGCGCCAGAAGACGGAGGTCCGCCCCCAGGCGATGCTCGAGGCGAAGGAT
2251 CTGCCCACGTCCCGGCTGTCCGAGTTTATTACGGAGCGCCTGAACCGCGA
2301 GCTGGAGAAGGAGCACCACAAGCGGGCTGAGCAGCAGGGCAAGCCGCTGC
2351 ACGAGGTGGCGAAGCCCGAGCCCCTGACCGTGCGGATGATCAACTCCGTG
2401 ATGAAGAAGTGCGAGGTCAAGCCGCGCTTCCACGAGACGTTCGGCCCCAC
2451 CGACGGCTACCCCGGGGAGTTCGGCTACCGGCAGAAGGTGCTGCTGCTGT
2501 TCCAAAGCCTGGACGGTGTCGACGTGTGCCTGTTCTGCATGTACGTGCAG
2551 GAGTACGGCAAGGACTGCCCTGCGCCCAACACCAACGTGGTGTACCTGTC
2601 GTATCTGGACTCCGTCAAGTACTTCCGCCCTGAGATTCCCTCGGCCCTGG
2651 GCCCTGCCGTGTCGCTGCGCACCTTCGTGTACCACCAACTCCTGATCGCC
2701 TACGTGGAGTTTACCCGCAACATGGGTTTTGAGCAGATGTACATTTGGGC
2751 GTGCCCGCCGATGCAAGGCGACGACTACATCCTGTACTGCCACCCGACCA
2801 AGCAGAAGACGCCGCGCTCGGACCGCCTGCGCATGTGGTACATTGAGATG
2851 CTGAAGCTGGCGAAGGAGGAGGGTATCGTGAAGCACCTGAGCACGCTGTG
2901 GGATACGTACTTCGAGGGCGGTCGCGACCACCGGATGGAGCGCTGCTCGG
2951 TCACGTACATTCCGTACATGGAGGGCGACTACTGGCCCGGCGAGGCTGAG
3001 AACCAGCTCATGGCCATTAACGACGCGGCCAAGGGCAAGCCTGGGACCAA
3051 GGGTGCGGGCAGCGCCCCGAGCCGCAAGGCCGGTGCCAAGGGCAAGCGCT
3101 ACGGCGGTGGCCCCGCCACGGCTGATGAGCAGCTGATGGCCCGCCTCGGT
3151 GAGATCCTGGGCGGGAACATGCGGGAGGACTTCATTGTGGTCCACATGCA
3201 GGTGCCCTGCACGTTCTGCCGCGCTCACATTCGGGGTCCGAACGTGGTGT
3251 ACCGCTATCGGACGCCGCCTGGCGCGACCCCTCCCAAGGCTGCCCCCGAG
3301 CGCAAGTTCGAGGGCATCAAGCTGGAGGGCGGTGGCCCCAGCGTGCCCGT
3351 GGGCACCGTCTCGAGCCTGACGATCTGCGAGGCGTGCTTTCGCGACGAGG
3401 AGACGCGCACGCTGACCGGCCAACAGCTGCGCCTGCCCGCTGGCGTGTCG
3451 ACCGCTGAGCTCGCGATGGAGAAGCTGGAGGAGATGATCCAGTGGGACCG
3501 CGACCCTGACGGCGACATGGAGAGCGAGTTCTTCGAGACGCGGCAGACCT
3551 TCCTGTCGCTGTGCCAGGGCAACCACTACCAGTTCGACACCCTCCGCCGC
```

-continued

```
3601  GCTAAGCACTCGTCGATGATGGTGCTCTACCACCTGCACAACCCCCACTC

3651  GCCGGCGTTCGCGTCCTCGTGCAACCAGTGCAACGCCGAGATCGAGCCGG

3701  GCAGCGGCTTTCGCTGCACCGTGTGCCCCGACTTCGACATGTGCGCCAGC

3751  TGCAAGGTCAACCCTCATAAGCGCGCCCTGGACGAGACGCGCCAGCGGCT

3801  GACCGAGGCCGAGCGCCGGGAGCGCAACGAGCAGCTGCAGAAGACCCTCG

3851  CCCTGCTGGTGCACGCCTGCGGCTGCCACAACAGCGCGTGCGGCTCCAAC

3901  AGCTGCCGCAAGGTGAAGCAGCTGTTCCAGCACGCGGTCCACTGCCAGAG

3951  CAAGGTGACCGGGGGCTGCCAGCTGTGCAAGAAGATGIGGTGCCTGCTGA

4001  ACCTGCACGCCAAGTCCTGCACCCGCGCGGACTGCCCGGTGCCGCGCTGC

4051  AAGGAGCTGAAGGAGCTGCGCCGGCGCCAAACGAACCGGCAGGAGGAGAA

4101  GCGCCGGGCGGCCTACGCCGCTATGCTGCGCAACCAGATGGCCGGCAGCC

4151  AGGCTCCGCGCCCCATGTAA.
```

LexA-p300 Fusion Protein (SEQ ID NO 2) is the respective protein sequence encoded by the nucleic acid sequence of SEQ ID NO 1. The LexA binding domain is the sequence up to and including amino acid 230 and the full-length p300 HAT domain sequence begins at amino acid 234. A 3-amino acid peptide linker (GVL) connects LexA binding domain and p300, which represents the DNA restriction site PpuMI (9 bp):

SEQ ID NO 2

```
   1  MKALTARQQEVFDLIRDHISQTGMPPTRAEIAQRLGFRSPNAAEEHLKAL

  51  ARKGVIEIVSGASRGIRLLQEEEEGLPLVGRVAAGEPLLAQQHIEGHYQV

 101  DPSLFKPNADFLLRVSGMSMKDIGIMDGDLLAVHKTQDVRNGQVVVARID

 151  DEVTVKRLKKQGNKVELLPENSEFKPIVVDLRQQSFTIEGLAVGVIRNGD

 201  WLEFPGIRRPWRPLESTCSQANSGRISYDLGVLMVPMGAPAMPMGNNGSP

 251  MLNGMGMFNAPQQTVPNGGPGGVNPMGQVPAMPAPIPNGGLPGMNAAGGA

 301  DDPAKQREQSIQKQQRWLLFLRHCAKCRAPGEDCQLKSQCKFGKQLWQHI

 351  LSCQNPACEYPRCTNSKDLLKHHQKCQEQTCPVCMPVKDYVKKTRQATQQ

 401  QQQMQQQQQIQQQQQQQMQQQQMQQQQLQQQQMQQQQQMQQQQQPGVGAN

 451  FMPTPPMMPNGMFPQQQPQQAMRLNANGLGGQKRPHEMMGMSSGGMDGMN

 501  QMVPVGGGGMGMSMPMGMNNPMQGGMPLQPPPQVQAPGQGPMMSAPQQQQ

 551  QQPAPKRAKTDDVLRQNTGTSLLETFDAKQIRVHVDLIRAAAVTQKAQQP

 601  PPANPDDACKVCALTKLSFEPPVIYCSSCGLRIKRGQIFYSTPPDHGNDL

 651  KGYFCHQCFTDQKGERILVEGVSIKKSDLVKRKNDEEIEEGWVQCDHCEG

 701  WVHQICGMFNKGRNNTDVHYLCPDCLAVGYERGQRQKTEVRPQAMLEAKD

 751  LPTSRLSEFITERLNRELEKEHHKRAEQQGKPLHEVAKPEPLTVRMINSV

 801  MKKCEVKPRFHETFGPTDGYPGEFGYRQKVLLLFQSLDGVDVCLFCMYVQ

 851  EYGKDCPAPNTNVVYLSYLDSVKYFRPEIPSALGPAVSLRTFVYHQLLIA

 901  YVEFTRNMGFEQMYIWACPPMQGDDYILYCHPTKQKTPRSDRLRMWYIEM

 951  LKLAKEEGIVKHLSTLWDTYFEGGRDHRMERCSVTYIPYMEGDYWPGEAE

1001  NQLMAINDAAKGKPGTKGAGSAPSRKAGAKGKRYGGGPATADEQLMARLG

1051  EILGGNMREDFIVVHMQVPCTFCRAHIRGPNVVYRYRIPPGATPPKAAPE

1101  RKFEGIKLEGGGPSVPVGTVSSLTICEACFRDEETRTLTGQQLRLPAGVS

1151  TAELAMEKLEEMIQWDRDPDGDMESEFFETRQTFLSLCQGNHYQFDTLRR
```

-continued

```
1201 AKHSSMMVLYHLHNPHSPAFASSCNQCNAEIEPGSGFRCTVCPDFDMCAS

1251 CKVNPHKRALDETRQRLTEAERRERNEQLQKTLALLVHACGCHNSACGSN

1301 SCRKVKQLFQHAVHCQSKVTGGCQLCKKMWCLLNLHAKSCTRADCPVPRC

1351 KELKELRRRQTNRQEEKRRAAYAAMLRNQMAGSQAPRPM*.
```

LexA-p300 HAT domain DNA (SEQ ID NO 3) is a nucleic acid sequence corresponding to a gene encoding the LexA binding domain-acetyl-transferase (HAT) domain of the Chlamy p300 protein. Similarly, the LexA binding domain is the sequence up to and including nucleotide 690 and the p300 HAT domain sequence begins at nucleotide 700. A 3-amino acid peptide linker (GVL) connects LexA binding domain and p300, which represents the DNA restriction site PpuMI (9 bp).

```
                                                      SEQ ID NO 3
   1 ATGAAGGCTCTCACCGCTCGCCAACAGGAGGTCTTTGATCTGATTCGCGA

  51 CCACATCTCGCAGACCGGCATGCCGCCGACCCGGGCGGAGATTGCTCAGC

 101 GGCTGGGCTTCCGGAGCCCCAACGCGGCCGAGGAGCACCTGAAGGCCCTC

 151 GCGCGCAAGGGGGTGATCGAGATTGTCTCCGGCGCTAGCCGCGGCATCCG

 201 CCTGCTGCAGGAGGAGGAGGAGGGCCTGCCGCTGGTCGGGCGGGTCGCGG

 251 CCGGGGAGCCTCTGCTGGCCCAGCAGCACATCGAGGGCCACTACCAAGTG

 301 GACCCCTCGCTGTTTAAGCCCAACGCGGACTTCCTGCTCCGGGTGTCGGG

 351 CATGAGCATGAAGGACATCGGCATCATGGACGGCGACCTCCTGGCGGTGC

 401 ACAAGACCCAGGACGTGCGCAACGGCCAGGTGGTCGTCGCGCGGATTGAC

 451 GACGAGGTGACCGTGAAGCGGCTGAAGAAGCAGGGCAACAAGGTCGAGCT

 501 GCTGCCCGAGAACTCGGAGTTCAAGCCTATCGTGGTCGACCTGCGCCAGC

 551 AGTCCTTCACCATCGAGGGCCTGGCCGTGGGGGTCATCCGCAACGGTGAC

 601 TGGCTGGAGTTCCCCGGCATCCGGCGCCCGTGGCGGCCGCTGGAGTCCAC

 651 CTGCAGCCAGGCGAACTCCGGCCGCATCTCCTACGATCTGGGGGTCCTTG

 701 AGGTGGCCAAGCCGGAGCCGCTGACCGTGCGGATGATCAACAGCGTGATG

 751 AAGAAGTGCGAGGTCAAGCCCCGCTTCCACGAGACGTTCGGTCCGACCGA

 801 CGGTTACCCCGGGGAGTTCGGCTACCGGCAGAAGGTGCTCCTCCTGTTCC

 851 AGTCCCTCGACGGCGTCGACGTGTGCCTGTTCTGCATGTACGTGCAGGAG

 901 TACGGGAAGGACTGCCCGGCGCCCAACACGAACGTGGTGTACCTGAGCTA

 951 CCTGGACTCCGTCAAGTATTTCCGCCCCGAGATTCCCAGCGCCCTGGGCC

1001 CTGCGGTGAGCCTGCGGACCTTCGTGTACCACCAGCTCCTGATTGCGTAC

1051 GTGGAGTTCACGCGCAACATGGGCTTCGAGCAGATGTACATTTGGGCGTG

1101 CCCCCCCATGCAGGGGGACGACTATATCCTGTATTGCCATCCCACGAAGC

1151 AGAAGACCCCGCGCTCGGACCGCCTGCGCATGTGGTACATCGAGATGCTG

1201 AAGCTGGCTAAGGAGGAGGGCATCGTGAAGCACCTGTCGACGCTGTGGGA

1251 CACCTACTTCGAGGGCGGTCGCGACCACCGGATGGAGCGCTGCAGCGTGA

1301 CCTACATCCCCTACATGGAGGGCGACTACTGGCCTGGCGAGGCCGAGTAA.
```

LexA-p300 HAT domain AA (SEQ ID NO 4) is an exemplary GEE protein sequence of a LexA binding domain-Chlamy p300 protein, where the Chlamy p300 is limited to the histone acetyl-transferase (HAT) domain of the Chlamy p300 enzyme. The LexA binding domain is the sequence up to and including amino acid 230 and the p300 HAT domain sequence begins at amino acid 234. The 3-amino acid peptide linker (GVL) connects LexA binding domain and p300:

```
                                                          SEQ ID NO 4
  1  MKALTARQQEVFDLIRDHISQTGMPPTRAEIAQRLGFRSPNAAEEHLKAL

 51  ARKGVIEIVSGASRGIRLLQEEEEGLPLVGRVAAGEPLLAQQHIEGHYQV

101  DPSLFKPNADFLLRVSGMSMKDIGIMDGDLLAVHKTQDVRNGQVVVARID

151  DEVTVKRLKKQGNKVELLPENSEFKPIVVDLRQQSFTIEGLAVGVIRNGD

201  WLEFPGIRRPWRPLESTCSQANSGRISYDLGVLEVAKPEPLTVRMINSVM

251  KKCEVKPRFHETFGPTDGYPGEFGYRQKVLLLFQSLDGVDVCLFCMYVQE

301  YGKDCPAPNTNVVYLSYLDSVKYFRPEIPSALGPAVSLRTFVYHQLLIAY

351  VEFTRNMGFEQMYIWACPPMQGDDYILYCHPTKQKTPRSDRLRMWYIEML

401  KLAKEEGIVKHLSTLWDTYFEGGRDHRMERCSVTYIPYMEGDYWPGEAE*.
```

Codon-optimized Venus gene sequence is a preferred embodiment:

```
                                                          SEQ ID NO 5
  1  ATGGTGTCGAAGGGTGAGGAGCTGTTTACCGGTGTCGTGCCTATTCTGGT

 51  GGAGCTCGACGGCGACGTCAACGGGCACAAGTTTTCGGTGTCCGGCGAGG

101  GTGAGGGGGACGCGACGTACGGCAAGCTCACGCTGAAGCTGATCTGCACC

151  ACCGGCAAGCTGCCCGTCCCCTGGCCGACGCTGGTGACCACCCTGGGCTA

201  CGGCCTGCAGTGCTTCGCCCGCTACCCGGACCACATGAAGCAGCACGACT

251  TCTTCAAGTCGGCCATGCCCGAGGGGTACGTGCAGGAGCGCACGATCTTC

301  TTTAAGGACGATGGCAACTACAAGACCCGCGCTGAGGTGAAGTTCGAGGG

351  CGATACGCTGGTGAACCGCATCGAGCTCAAGGGCATCGACTTCAAGGAGG

401  ACGGCAACATCCTGGGTCACAAGCTGGAGTACAACTACAACTCCCACAAC

451  GTGTACATCACGGCGGATAAGCAGAAGAACGGCATCAAGGCCAACTTTAA

501  GATTCGCCATAACATCGAGGACGGCGGCGTGCAGCTCGCCGACCACTACC

551  AGCAGAACACCCCGATCGGCGACGGCCCCGTGCTGCTGCCCGATAACCAC

601  TACCTCAGCTACCAGTCGGCCCTGTCCAAGGATCCCAACGAGAAGCGCGA

651  TCACATGGTCCTCCTGGAGTTCGTGACCGCCGCTGGCATCACCCTGGGCA

701  TGGACGAGCTGTACAAGTAA.
```

SEQ ID NO 6 is the protein encoded by the nucleic acid of SEQ ID NO 5. The Venus AA sequence:

```
                                                          SEQ ID NO 6
  1  MVSKGEELFTGVVPILVELDGDVNGHKFSVSGEGEGDATYGKLTLKLICT

 51  TGKLPVPWPTLVTTLGYGLQCFARYPDHMKQHDFFKSAMPEGYVQERTIF

101  FKDDGNYKTRAEVKFEGDTLVNRIELKGIDFKEDGNILGHKLEYNYNSHN

151  VYITADKQKNGIKANFKIRHNIEDGGVQLADHYQQNTPIGDGPVLLPDNH

201  YLSYQSALSKDPNEKRDHMVLLEFVTAAGITLGMDELYK*.
```

SEQ ID NO 7 is a nucleic acid encoding a Venus-Bcl-$x_L$ fusion of the invention. It was designed to represent preferred codon usage in algae. The sequence up to and including nucleotide 717 represents Venus. A 3-amino acid peptide linker (CVL) connects Venus and Bcl-$x_L$, which represents the DNA restriction site PpuMI (9 bp). Bcl-$x_L$ begins at nucleotide 726.

```
                                                   SEQ ID NO 7
   1  ATGGTGTCGAAGGGTGAGGAGCTGTTTACCGGTGTCGTGCCTATTCTGGT
  51  GGAGCTCGACGGCGACGTCAACGGGCACAAGTTTTCGGTGTCCGGCGAGG
 101  GTGAGGGGGACGCGACGTACGGCAAGCTCACGCTGAAGCTGATCTGCACC
 151  ACCGGCAAGCTGCCCGTCCCCTGGCCGACGCTGGTGACCACCCTGGGCTA
 201  CGGCCTGCAGTGCTTCGCCCGCTACCCGGACCACATGAAGCAGCACGACT
 251  TCTTCAAGTCGGCCATGCCCGAGGGGTACGTGCAGGAGCGCACGATCTTC
 301  TTTAAGGACGATGGCAACTACAAGACCCGCGCTGAGGTGAAGTTCGAGGG
 351  CGATACGCTGGTGAACCGCATCGAGCTCAAGGGCATCGACTTCAAGGAGG
 401  ACGGCAACATCCTGGGTCACAAGCTGGAGTACAACTACAACTCCCACAAC
 451  GTGTACATCACGGCGGATAAGCAGAAGAACGGCATCAAGGCCAACTTTAA
 501  GATTCGCCATAACATCGAGGACGGCGGCGTGCAGCTCGCCGACCACTACC
 551  AGCAGAACACCCCGATCGGCGACGGCCCCGTGCTGCTGCCCGATAACCAC
 601  TACCTCAGCTACCAGTCGGCCCTGTCCAAGGATCCCAACGAGAAGCGCGA
 651  TCACATGGTCCTCCTGGAGTTCGTGACCGCCGCTGGCATCACCCTGGGCA
 701  TGGACGAGCTGTACAAGGGGGTCCTTATGAGCCAGAGCAACCGGGAGCTG
 751  GTGGTGGACTTCCTGAGCTACAAGCTGAGCCAAAAGGGCTATAGCTGGTC
 801  GCAGTTCTCCGACGTCGAGGAGAACCGGACCGAGGCCCCCGAGGGGACCG
 851  AGTCCGAGATGGAGACGCCGAGCGCGATTAACGGCAACCCGAGCTGGCAC
 901  CTGGCGGACTCCCCTGCCGTGAACGGCGCGACCGGCCACAGCTCCAGCCT
 951  GGACGCGCGCGAGGTCATCCCGATGGCGGCCGTGAAGCAGGCCCTCCGCG
1001  AGGCCGGCGACGAGTTCGAGCTGCGCTATCGCCGCGCTTTCTCGGACCTG
1051  ACCAGCCAGCTGCACATCACCCCCGGCACGGCTTACCAAAGCTTCGAGCA
1101  GGTGGTGAACGAGCTGTTCCGCGACGGCGTGAACTGGGGTCGCATCGTGG
1151  CGTTCTTCAGCTTCGGCGGTGCGCTGTGCGTGGAGAGCGTCGACAAGGAG
1201  ATGCAGGTGCTGGTGTCGCGCATTGCGGCTTGGATGGCCACCTACCTGAA
1251  CGACCACCTGGAGCCCTGGATTCAGGAGAACGGCGGCTGGGACACCTTCG
1301  TCGAGCTGTACGGCAACAACGCTGCGGCGGAGAGCCGCAAGGGCCAAGAG
1351  CGGTTCAACCGCTGGTTCCTCACGGGGATGACCGTGGCGGGCGTCGTCCT
1401  GCTGGGCAGCCTGTTCTCGCGGAAGTAA.
```

Venus-Bcl-$x_L$ Protein (SEQ ID NO 8) is the protein fusion encoded by the nucleic acid of SEQ ID NO 7. The underlying Bcl-$x_L$ protein sequence (233 AA) is encoded by the DNA sequence GenBank ID: 20336334 from NCBI Database:

```
                                                   SEQ ID NO 8
   1  MVSKGEELFTGVVPILVELDGDVNGHKFSVSGEGEGDATYGKLTLKLICT
  51  TGKLPVPWPTLVTTLGYGLQCFARYPDHMKQHDFFKSAMPEGYVQERTIF
 101  FKDDGNYKTRAEVKFEGDTLVNRIELKGIDFKEDGNILGHKLEYNYNSHN
 151  VYITADKQKNGIKANFKIRHNIEDGGVQLADHYQQNTPIGDGPVLLPDNH
```

-continued

```
201   YLSYQSALSKDPNEKRDHMVLLEFVTAAGITLGMDELYKGVLMSQSNREL

251   VVDFLSYKLSQKGYSWSQFSDVEENRTEAPEGTESEMETPSAINGNPSWH

301   LADSPAVNGATGHSSSLDAREVIPMAAVKQALREAGDEFELRYRRAFSDL

351   TSQLHITPGTAYQSFEQVVNELFRDGVNWGRIVAFFSFGGALCVESVDKE

401   MQVLVSRIAAWMATYLNDHLEPWIQENGGWDTFVELYGNNAAAESRKGQE

451   RFNRWFLTGMTVAGVVLLGSLFSRK*.
```

Example 1

An Exemplary Vector of the Invention

FIG. 1 illustrates a construct in accordance to the invention. The starting vector is pSP124. See V. Lumbreras, D. R. S. and S. Purton, Plant J., 14(4):441-447 (1998). Features of the vector are listed in FIG. 1, i.e. the two regions indicated in FIG. 1 to be part of the backbone vector, pSP124.

None pSP124 sequences are preferably engineered as individual synthetic DNA fragments and strung together via restriction enzyme sites, by well-known techniques. Alternative approaches and mixtures of approaches are available. For example, some features are optionally introduced as PCR products or "cut and pasted" from other available constructs. Typically, sequencing and/or other assays (e.g. size analysis, hybridization) are used to verify the resultant vector.

As an example, one section of the insert is created by synthesis of a region having a BamHI site and ending with an EcoRI site ("Synthetic_1"). This region provides a transcriptional enhancer region, two LexA binding motifs, a rubisco transcriptional promoter (including the first intron of rbcS2), a YFP-Bcl-$x_L$ fusion protein, and a rubisco 3'UTR. The YFP and Bcl-$x_L$ coding regions were designed in this instance to reflect the preferred codon usage in algae.

Another region incorporated is prepared by high fidelity PCR and effectively provides the p300 (HAT) gene ("Genomic PCR"). Flanking the genomic PCR fragment are two additional regions prepared by synthetic DNA ("Synthetic_2"). The region transcriptionally upstream of the p300 gene provides the LexA binding domain coding sequence downstream of transcriptional promoters and two LexA binding sites. The Synthetic_2 region provides a 3'UTR. Combined, the Synthetic_2 and Genomic regions create a complete transcription unit encoding a LexA-p300 fusion protein (GEE).

Effectively, FIG. 1 and these explanations provide an example of the features of a construct of the invention and illustrate methods of creating the features within an algae compatible plasmid. Two transcriptional units face opposing directions and each have two LexA binding sites, creating an opportunity for the LexA-p300 to bind at any of four sites and affect transcription levels of either transcriptional unit. A third transcriptional unit provides a selection marker, bleomycin-resistance.

It will be recognized by a skilled artisan that other design approaches are available, including the incorporation within the vector of additional or different genes incorporated for expression, different gene expression control features, other restriction sites, change the number of LexA-BS, and so on, without changing the concept behind the creation of this vector, namely to effectively increase the levels of expression of the genes located in vicinity of a DNA-BS, in the presence of a GEE that recognizes/binds the BS.

Example 2

Additional Exemplary Vectors

Two vectors are constructed which are in most respects identical, but for the presence of a GEE unit. The vectors are otherwise the same to each other and similar to the vector of FIG. 2A. The use of these vectors in parallel allows testing of the p300 activity and the role of LexA in otherwise identical genetic backgrounds. The use of two vectors also allows for modulation of the GEE activities by such additional engineering, for example, as addition of other genes, addition of multiple copies of GEE and so on.

Notably, "LexA BS" does not refer to any limit of the number of binding sites; anything from one BS to many BS are possibly located at the indicated position. Practically speaking, it is unlikely to utilize more than about 8 BS, as benefit from additional sites would be unlikely. Preferably, about 2 to 6 BS are located in the region at or near the 5' end of genes desirably expressed, more preferably there are 2-4 BS.

Example 3

Characterization of GEE Efficacy with a Bidirectional Promoter

Experiment 1. Use the bidirectional construct with YFP reporter in the position of the GOI and either one of two variants of the GEE construct: [1] in which the LexA-p300 chimeric gene is driven in the opposite direction (FIG. 1) or [2] in which only LexA is driven in the opposite direction which serves as a control.

Algae are transformed with the two constructs and selected on appropriate antibiotic containing selection media (e.g. media containing bleocin). After selection, 100 colonies from transformation for each construct are chosen to analyze the expression of the YFP transgene by assaying mRNA expression using rtPCR, protein expression with Western blot, and single cell fluorescence by flow cytometry and fluorescent microscopy. The clonal populations are passaged for 2, 4, 6, and 10 generations. The frequency of high-level expression of YFP are compared between the LexA-p300 and LexA only clones. The LexA-p300 GEE increases expression and maintains a higher level of nuclear transgene expression over time.

Example 4

Characterization of GEE Efficacy Using Distinct Plasmids

Figure 2B:
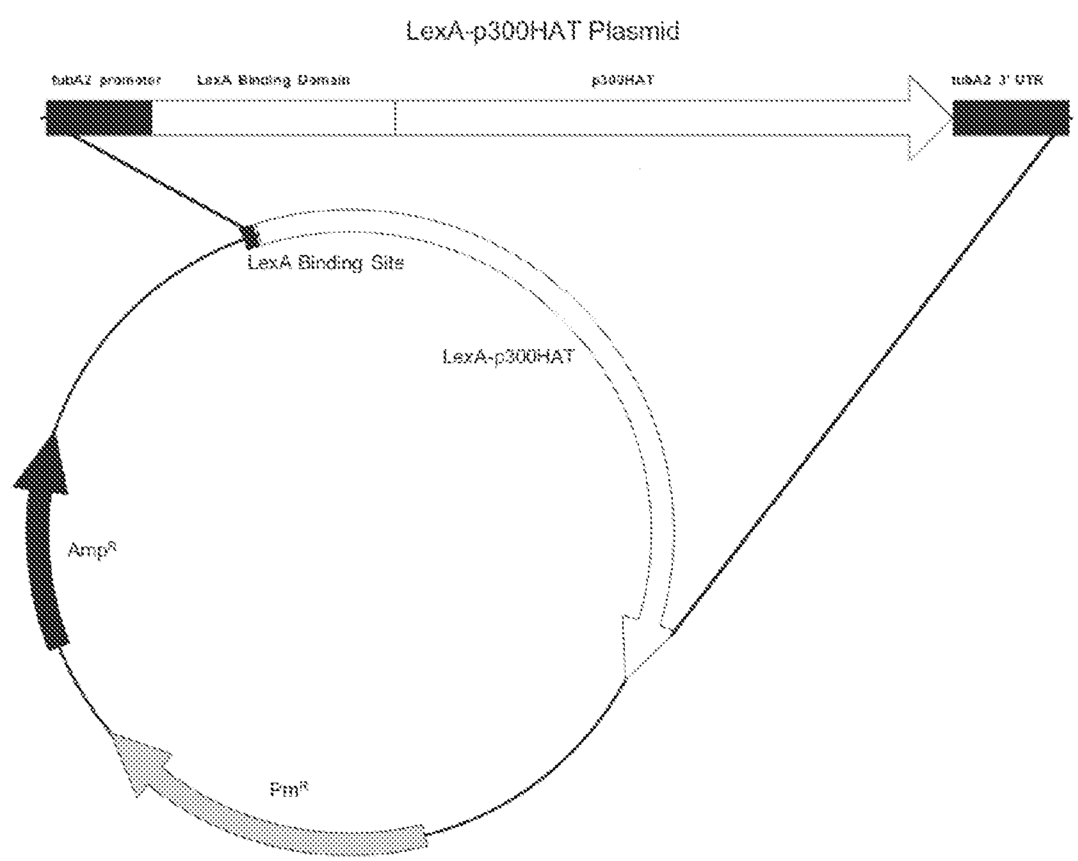

Generate two sets of stable clones: Set one is a stable cell line with the incorporated transgene encoding the LexA-p300 fusion (FIG. 2A) that is then transformed with a plasmid that expresses the YFP vector (FIG. 2B). Set two is a stable cell line with the incorporated transgene encoding the LexA only (related to FIG. 2A with the exception of the p300 fusion partner) that is then transformed with a plasmid that expresses the YFP vector (FIG. 2B).

Select for stable cell lines and characterize the YFP expression over time by assaying mRNA expression by rtPCR, western blot to determine protein expression, and assay of single cell fluorescence by flow cytometry and fluorescent microscopy. The clonal populations will be passaged for 2, 4, 6, and 10 generations. Similarly, the frequency of high-level expression of YFP are compared between the LexA-p300 and LexA only clones. The LexA-p300 GEE increases expression and maintains a higher level of nuclear transgene expression over time.

The invention described above should be read in conjunction with the accompanying claims and drawings. The description of embodiments and examples enable one to practice various implementations of the invention and they are not intended to limit the invention to the preferred embodiment, but to serve as a particular example of the invention. Those skilled in the art will appreciate that they may readily use the conception and specific embodiments disclosed as a basis for modifying or designing other methods and systems for carrying out the same purposes of the present invention.

All references, including publications, patent applications, patents, and website content cited herein are hereby incorporated by reference to the same extent as if each reference were individually and specifically indicated to be incorporated by reference and was set forth in its entirety herein.

The websites mentioned herein were last visited on Oct. 30, 2010.

The use of the terms "a" and "an" and "the" and similar references in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. NO language in the specification should be construed as indicating any non-claimed element as essential to the practice of the invention.

What is claimed is:

1. A construct for enhanced gene expression in an alga cell, comprising:

a eukaryotic unicellular algae compatible transcriptional promoter functionally upstream of a coding sequence for a gene expression enhancer (GEE) fusion protein, wherein the fusion protein comprises an algae derived p300 functionally fused to the DNA binding protein, wherein at least the portion of the coding sequence of the DNA binding protein domain is codon optimized for improved expression in a eukaryotic unicellular algae;

at least one transgene functionally downstream of a eukaryotic unicellular algae compatible transcriptional promoter; and at least one DNA region that is a binding site for the DNA binding protein, in vicinity of at least one of said transcriptional promoters.

2. The construct of claim 1, wherein the DNA binding protein is LexA DNA Binding domain.

3. The construct of claim 1, wherein the p300 part of the GEE fusion protein is from *Chlamydomonas reinhardtii.*

4. The construct of claim 1, wherein only a HAT domain of the p300 protein is part of the GEE fusion protein.

5. The construct of claim 1, wherein the transgene is codon modified for improved expression in algae.

6. The construct of claim 5, wherein the transgene is a fluorescence-Bcl-$x_L$ fusion gene.

7. The construct of claim 6, wherein the fluorescence-Bcl-$x_L$ fusion gene is a YFP-Bcl-$x_L$ fusion.

8. The construct of claim 6, wherein the fluorescence-Bcl-$x_L$ fusion gene is a Venus-Bcl-$x_L$ fusion.

9. The construct of claim 1, further comprising at least one selective marker.

10. The construct of claim 9, wherein the GEE fusion protein and the at least one transgene are introduced into the system on one vector and structurally arranged to be expressed from one bidirectional promoter region and comprising DNA binding sites in the vicinity of both promoters.

11. The construct of claim 9, wherein the GEE fusion protein and the transgene are introduced in the system on separate vectors, each comprising a selective marker and the selective markers are not the same.

12. The construct of claim 1, wherein the algae compatible transcriptional promoters are hsp70, rbcS, nitA, tubA2 or a combination thereof.

13. The construct of claim 1, wherein the GEE fusion protein comprises a DNA binding domain functionally fused to an algae derived p300 homologue having at least 80% identity over the HAT region to the p300 from *Chlamydomonas reinhardtii*.

14. The construct claim 13, wherein the GEE fusion protein comprises a DNA binding domain functionally fused to the HAT domain from an algae derived p300 homologue, the homologue having at least 80% identity over the HAT region to the p300 from *Chlamydomonas reinhardtii*.

15. A method of expressing a gene in an alga cell at higher levels, comprising:

transforming eukaryotic unicellular algae with at least one vector comprising:

a eukaryotic unicellular algae compatible transcriptional promoter functionally upstream of a coding sequence for a gene expression enhancer (GEE) fusion protein, wherein the fusion protein comprises an algae derived p300 functionally fused to the DNA binding protein, wherein at least the portion of the coding sequence of the DNA binding protein domain is codon optimized for improved expression in a eukaryotic unicellular algae;

at least one transgene functionally downstream of a eukaryotic unicellular algae compatible transcriptional promoter; and at least one DNA region that is a binding site for the DNA binding protein, in vicinity of at least one of said transcriptional promoters;

selecting a transformed algae cell; and detecting the expression of said GEE gene or said transgene in said algae.

16. The method of claim 15, wherein said DNA Binding protein is the LexA binding domain.

17. The method of claim 15, wherein the p300 is from *Chlamydomonas reinhardtii*.

18. The method of claim 17, wherein the GEE fusion protein comprises the LexA binding domain functionally fused with the HAT domain of the p300 protein from *Chlamydomonas reinhardtii*.

19. The method of claim 17, wherein said transgene is a YFP-Bcl-$x_L$ fusion protein or a Venus-Bcl-$x_L$ fusion protein.

20. The method of claim 15, wherein said GEE fusion protein and said transgene are transformed in algae on separate vectors, first selecting a vector stably expressing the GEE fusion protein and then transforming the selected algae with the vector comprising the transgene.

* * * * *

SEQUENCE LISTING

```
<160> NUMBER OF SEQ ID NOS: 11

<210> SEQ ID NO 1
<211> LENGTH: 4170
<212> TYPE: DNA
<213> ORGANISM: Artificial Sequence
<220> FEATURE:
<223> OTHER INFORMATION: LexA-p300 Fusion

<400> SEQUENCE: 1

atgaaggctc tgaccgctcg ccagcaggag gtgtttgatc tgattcggga ccatatcagc     60

caaacgggca tgcccccctac gcgcgcggag atcgcgcaac ggctgggctt ccgctccccg    120

aacgcggctg aggagcacct gaaggcgctg gcgcgcaagg gtgtgattga gatcgtctcc    180

ggcgcgtcgc ggggcattcg gctgctgcag gaggaggagg agggtctgcc tctggtgggg    240

cgggtggctg cgggcgagcc cctgctggcc cagcagcaca ttgagggcca ctaccaagtg    300

gacccgtccc tcttcaagcc gaacgccgat ttcctgctgc gcgtcagcgg tatgagcatg    360

aaggacatcg gcatcatgga cggtgacctg ctggccgtgc ataagacgca ggacgtgcgc    420

aacggccaag tggtcgtcgc ccgcatcgat gacgaggtga ccgtgaagcg cctgaagaag    480

caggggaaca aggtcgagct gctgcccgag aacagcgagt tcaagcccat cgtggtggat    540

ctgcgccagc aatccttcac catcgagggc ctggcggtgg gcgtgatccg caacggcgac    600

tggctggagt tcccgggcat ccgccgcccg tggcgccctc tggagtccac gtgctcgcag    660

gccaactccg gccgcattag ctacgacctg ggggtcctta tggtgccgat gggcgcgccc    720

gctatgccca tgggcaacaa cggctcgccc atgctgaacg gcatgggtat gttcaacgcc    780

ccgcagcaga ccgtgcccaa cggcgggccg ggtggcgtga accccatggg ccaggtgccg    840

gcgatgcctg cgccgatccc caacggcggt ctgcccggta tgaacgctgc cggcggtgcc    900

gacgatcctg cgaagcagcg ggagcaatcg atccagaagc agcagcgctg gctgctgttc    960

ctgcggcact gcgcgaagtg ccgggctccc ggcgaggact gccagctgaa gtcccagtgc   1020
```

-continued

```
aagttcggca agcagctgtg gcagcacatc ctgtcgtgcc aaaacccggc ctgcgagtac   1080
ccgcgctgca ccaactccaa ggatctgctc aagcaccacc agaagtgcca ggagcagacc   1140
tgccccgtgt gcatgccggt gaaggactac gtgaagaaga cgcgccaggc gacccaacag   1200
cagcaacaaa tgcagcaaca acagcaaatc cagcaacagc aacaacaaca aatgcaacag   1260
caacagatgc aacagcagca gctccagcag cagcagatgc aacaacaaca gcagatgcag   1320
cagcagcaac agcccggcgt gggcgccaac ttcatgccca ccccgcccat gatgccgaac   1380
ggcatgttcc ctcaacagca gccccagcag gcgatgcgcc tgaacgccaa cggcctcggc   1440
ggccagaagc gcccccacga gatgatgggt atgtccagcg gcggcatgga cggtatgaac   1500
cagatggtgc ccgtcggcgg cggcggcatg ggcatgtcga tgccgatggg tatgaacaac   1560
cccatgcagg gcggtatgcc cctgcagcct ccgccccagg tgcaggctcc cggtcagggc   1620
cccatgatga gcgcccctca gcagcaacag cagcaaccgg cccctaagcg ggcgaagacc   1680
gacgatgtgc tgcgccagaa cacgggcacc agcctcctgg agacgttcga cgccaagcag   1740
atccgcgtgc acgtggacct gatccgcgct gccgcggtga cccagaaggc ccagcagcct   1800
cccccggcta accccgacga cgcgtgcaag gtctgcgcgc tgacgaagct gtcgttcgag   1860
cccccggtga tttactgctc gagctgcggc ctgcgcatca agcgcggcca gatcttctac   1920
agcacgcctc cggaccacgg caacgacctg aagggttact tctgccacca gtgcttcacc   1980
gaccagaagg gcgagcgcat cctggtggag ggcgtctcga tcaagaagag cgacctggtg   2040
aagcgcaaga acgatgagga gatcgaggag gggtgggtgc agtgcgacca ctgcgagggc   2100
tgggtgcacc agatttgcgg catgttcaac aagggccgga acaacacgga cgtccactac   2160
ctgtgccctg actgcctggc cgtgggctac gagcgcggcc agcgccagaa gacggaggtc   2220
cgcccccagg cgatgctcga ggcgaaggat ctgcccacgt cccggctgtc cgagtttatt   2280
acggagcgcc tgaaccgcga gctggagaag gagcaccaca agcgggctga gcagcagggc   2340
aagccgctgc acgaggtggc gaagcccgag cccctgaccg tgcggatgat caactccgtg   2400
atgaagaagt gcgaggtcaa gccgcgcttc cacgagacgt tcggccccac cgacggctac   2460
cccggggagt tcggctaccg gcagaaggtg ctgctgctgt tccaaagcct ggacggtgtc   2520
gacgtgtgcc tgttctgcat gtacgtgcag gagtacggca aggactgccc tgcgcccaac   2580
accaacgtgg tgtacctgtc gtatctggac tccgtcaagt acttccgccc tgagattccc   2640
tcggccctgg gccctgccgt gtcgctgcgc accttcgtgt accaccaact cctgatcgcc   2700
tacgtggagt ttacccgcaa catgggtttt gagcagatgt acatttgggc gtgcccgccg   2760
atgcaaggcg acgactacat cctgtactgc cacccgacca agcagaagac gccgcgctcg   2820
gaccgcctgc gcatgtggta cattgagatg ctgaagctgg cgaaggagga gggtatcgtg   2880
aagcacctga gcacgctgtg ggatacgtac ttcgagggcg gtcgcgacca ccggatggag   2940
cgctgctcgg tcacgtacat tccgtacatg gagggcgact actggcccgg cgaggctgag   3000
aaccagctca tggccattaa cgacgcggcc aagggcaagc ctgggaccaa gggtgcgggc   3060
agcgccccga gccgcaaggc cggtgccaag ggcaagcgct acggcggtgg ccccgccacg   3120
gctgatgagc agctgatggc ccgcctcggt gagatcctgg gcgggaacat gcgggaggac   3180
ttcattgtgg tccacatgca ggtgccctgc acgttctgcc gcgctcacat tcggggtccg   3240
aacgtggtgt accgctatcg gacgccgcct ggcgcgaccc ctcccaaggc tgcccccgag   3300
cgcaagttcg agggcatcaa gctggagggc ggtggcccca gcgtgcccgt gggcaccgtc   3360
tcgagcctga cgatctgcga ggcgtgcttt cgcgacgagg agacgcgcac gctgaccggc   3420
```

```
caacagctgc gcctgcccgc tggcgtgtcg accgctgagc tcgcgatgga gaagctggag   3480

gagatgatcc agtgggaccg cgaccctgac ggcgacatgg agagcgagtt cttcgagacg   3540

cggcagacct tcctgtcgct gtgccagggc aaccactacc agttcgacac cctccgccgc   3600

gctaagcact cgtcgatgat ggtgctctac cacctgcaca acccccactc gccggcgttc   3660

gcgtcctcgt gcaaccagtg caacgccgag atcgagccgg gcagcggctt tcgctgcacc   3720

gtgtgccccg acttcgacat gtgcgccagc tgcaaggtca accctcataa gcgcgccctg   3780

gacgagacgc gccagcggct gaccgaggcc gagcgccggg agcgcaacga gcagctgcag   3840

aagaccctcg ccctgctggt gcacgcctgc ggctgccaca acagcgcgtg cggctccaac   3900

agctgccgca aggtgaagca gctgttccag cacgcggtcc actgccagag caaggtgacc   3960

gggggctgcc agctgtgcaa gaagatgtgg tgcctgctga acctgcacgc caagtcctgc   4020

acccgcgcgg actgcccggt gccgcgctgc aaggagctga aggagctgcg ccggcgccaa   4080

acgaaccggc aggaggagaa gcgccgggcg gcctacgccg ctatgctgcg caaccagatg   4140

gccggcagcc aggctccgcg ccccatgtaa                                     4170
```

<210> SEQ ID NO 2
<211> LENGTH: 1389
<212> TYPE: PRT
<213> ORGANISM: Artificial Sequence
<220> FEATURE:
<223> OTHER INFORMATION: LexA-p300 Fusion

<400> SEQUENCE: 2

```
Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Glu Gly Leu Pro Leu Val Gly
65                  70                  75                  80

Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
        115                 120                 125

Asp Leu Leu Ala Val His Lys Thr Gln Asp Val Arg Asn Gly Gln Val
    130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
            180                 185                 190

Val Gly Val Ile Arg Asn Gly Asp Trp Leu Glu Phe Pro Gly Ile Arg
        195                 200                 205

Arg Pro Trp Arg Pro Leu Glu Ser Thr Cys Ser Gln Ala Asn Ser Gly
    210                 215                 220

Arg Ile Ser Tyr Asp Leu Gly Val Leu Met Val Pro Met Gly Ala Pro
225                 230                 235                 240
```

```
Ala Met Pro Met Gly Asn Asn Gly Ser Pro Met Leu Asn Gly Met Gly
                245                 250                 255

Met Phe Asn Ala Pro Gln Gln Thr Val Pro Asn Gly Gly Pro Gly Gly
            260                 265                 270

Val Asn Pro Met Gly Gln Val Pro Ala Met Pro Ala Pro Ile Pro Asn
        275                 280                 285

Gly Gly Leu Pro Gly Met Asn Ala Ala Gly Gly Ala Asp Asp Pro Ala
    290                 295                 300

Lys Gln Arg Glu Gln Ser Ile Gln Lys Gln Gln Arg Trp Leu Leu Phe
305                 310                 315                 320

Leu Arg His Cys Ala Lys Cys Arg Ala Pro Gly Glu Asp Cys Gln Leu
                325                 330                 335

Lys Ser Gln Cys Lys Phe Gly Lys Gln Leu Trp Gln His Ile Leu Ser
            340                 345                 350

Cys Gln Asn Pro Ala Cys Glu Tyr Pro Arg Cys Thr Asn Ser Lys Asp
        355                 360                 365

Leu Leu Lys His His Gln Lys Cys Gln Glu Gln Thr Cys Pro Val Cys
    370                 375                 380

Met Pro Val Lys Asp Tyr Val Lys Lys Thr Arg Gln Ala Thr Gln Gln
385                 390                 395                 400

Gln Gln Gln Met Gln Gln Gln Gln Gln Ile Gln Gln Gln Gln Gln Gln
                405                 410                 415

Gln Met Gln Gln Gln Gln Met Gln Gln Gln Gln Leu Gln Gln Gln Gln
            420                 425                 430

Met Gln Gln Gln Gln Gln Met Gln Gln Gln Gln Gln Pro Gly Val Gly
        435                 440                 445

Ala Asn Phe Met Pro Thr Pro Pro Met Met Pro Asn Gly Met Phe Pro
    450                 455                 460

Gln Gln Gln Pro Gln Gln Ala Met Arg Leu Asn Ala Asn Gly Leu Gly
465                 470                 475                 480

Gly Gln Lys Arg Pro His Glu Met Met Gly Met Ser Ser Gly Gly Met
                485                 490                 495

Asp Gly Met Asn Gln Met Val Pro Val Gly Gly Gly Gly Met Gly Met
            500                 505                 510

Ser Met Pro Met Gly Met Asn Asn Pro Met Gln Gly Gly Met Pro Leu
        515                 520                 525

Gln Pro Pro Pro Gln Val Gln Ala Pro Gly Gln Gly Pro Met Met Ser
    530                 535                 540

Ala Pro Gln Gln Gln Gln Gln Gln Pro Ala Pro Lys Arg Ala Lys Thr
545                 550                 555                 560

Asp Asp Val Leu Arg Gln Asn Thr Gly Thr Ser Leu Leu Glu Thr Phe
                565                 570                 575

Asp Ala Lys Gln Ile Arg Val His Val Asp Leu Ile Arg Ala Ala Ala
            580                 585                 590

Val Thr Gln Lys Ala Gln Gln Pro Pro Pro Ala Asn Pro Asp Asp Ala
        595                 600                 605

Cys Lys Val Cys Ala Leu Thr Lys Leu Ser Phe Glu Pro Pro Val Ile
    610                 615                 620

Tyr Cys Ser Ser Cys Gly Leu Arg Ile Lys Arg Gly Gln Ile Phe Tyr
625                 630                 635                 640

Ser Thr Pro Pro Asp His Gly Asn Asp Leu Lys Gly Tyr Phe Cys His
                645                 650                 655

Gln Cys Phe Thr Asp Gln Lys Gly Glu Arg Ile Leu Val Glu Gly Val
```

```
            660                 665                 670

Ser Ile Lys Lys Ser Asp Leu Val Lys Arg Lys Asn Asp Glu Glu Ile
        675                 680                 685

Glu Glu Gly Trp Val Gln Cys Asp His Cys Glu Gly Trp Val His Gln
    690                 695                 700

Ile Cys Gly Met Phe Asn Lys Gly Arg Asn Asn Thr Asp Val His Tyr
705                 710                 715                 720

Leu Cys Pro Asp Cys Leu Ala Val Gly Tyr Glu Arg Gly Gln Arg Gln
                725                 730                 735

Lys Thr Glu Val Arg Pro Gln Ala Met Leu Glu Ala Lys Asp Leu Pro
            740                 745                 750

Thr Ser Arg Leu Ser Glu Phe Ile Thr Glu Arg Leu Asn Arg Glu Leu
        755                 760                 765

Glu Lys Glu His His Lys Arg Ala Glu Gln Gln Gly Lys Pro Leu His
    770                 775                 780

Glu Val Ala Lys Pro Glu Pro Leu Thr Val Arg Met Ile Asn Ser Val
785                 790                 795                 800

Met Lys Lys Cys Glu Val Lys Pro Arg Phe His Glu Thr Phe Gly Pro
                805                 810                 815

Thr Asp Gly Tyr Pro Gly Glu Phe Gly Tyr Arg Gln Lys Val Leu Leu
            820                 825                 830

Leu Phe Gln Ser Leu Asp Gly Val Asp Val Cys Leu Phe Cys Met Tyr
        835                 840                 845

Val Gln Glu Tyr Gly Lys Asp Cys Pro Ala Pro Asn Thr Asn Val Val
    850                 855                 860

Tyr Leu Ser Tyr Leu Asp Ser Val Lys Tyr Phe Arg Pro Glu Ile Pro
865                 870                 875                 880

Ser Ala Leu Gly Pro Ala Val Ser Leu Arg Thr Phe Val Tyr His Gln
                885                 890                 895

Leu Leu Ile Ala Tyr Val Glu Phe Thr Arg Asn Met Gly Phe Glu Gln
            900                 905                 910

Met Tyr Ile Trp Ala Cys Pro Pro Met Gln Gly Asp Asp Tyr Ile Leu
        915                 920                 925

Tyr Cys His Pro Thr Lys Gln Lys Thr Pro Arg Ser Asp Arg Leu Arg
    930                 935                 940

Met Trp Tyr Ile Glu Met Leu Lys Leu Ala Lys Glu Glu Gly Ile Val
945                 950                 955                 960

Lys His Leu Ser Thr Leu Trp Asp Thr Tyr Phe Glu Gly Gly Arg Asp
                965                 970                 975

His Arg Met Glu Arg Cys Ser Val Thr Tyr Ile Pro Tyr Met Glu Gly
            980                 985                 990

Asp Tyr Trp Pro Gly Glu Ala Glu  Asn Gln Leu Met Ala  Ile Asn Asp
        995                 1000                1005

Ala Ala  Lys Gly Lys Pro Gly  Thr Lys Gly Ala Gly  Ser Ala Pro
    1010                1015                1020

Ser Arg  Lys Ala Gly Ala Lys  Gly Lys Arg Tyr Gly  Gly Gly Pro
    1025                1030                1035

Ala Thr  Ala Asp Glu Gln Leu  Met Ala Arg Leu Gly  Glu Ile Leu
    1040                1045                1050

Gly Gly  Asn Met Arg Glu Asp  Phe Ile Val Val His  Met Gln Val
    1055                1060                1065

Pro Cys  Thr Phe Cys Arg Ala  His Ile Arg Gly Pro  Asn Val Val
    1070                1075                1080
```

```
Tyr Arg  Tyr Arg Thr Pro Pro  Gly Ala Thr Pro Pro  Lys Ala Ala
    1085                 1090                 1095

Pro Glu  Arg Lys Phe Glu Gly  Ile Lys Leu Glu Gly  Gly Gly Pro
    1100                 1105                 1110

Ser Val  Pro Val Gly Thr Val  Ser Ser Leu Thr Ile  Cys Glu Ala
    1115                 1120                 1125

Cys Phe  Arg Asp Glu Glu Thr  Arg Thr Leu Thr Gly  Gln Gln Leu
    1130                 1135                 1140

Arg Leu  Pro Ala Gly Val Ser  Thr Ala Glu Leu Ala  Met Glu Lys
    1145                 1150                 1155

Leu Glu  Glu Met Ile Gln Trp  Asp Arg Asp Pro Asp  Gly Asp Met
    1160                 1165                 1170

Glu Ser  Glu Phe Phe Glu Thr  Arg Gln Thr Phe Leu  Ser Leu Cys
    1175                 1180                 1185

Gln Gly  Asn His Tyr Gln Phe  Asp Thr Leu Arg Arg  Ala Lys His
    1190                 1195                 1200

Ser Ser  Met Met Val Leu Tyr  His Leu His Asn Pro  His Ser Pro
    1205                 1210                 1215

Ala Phe  Ala Ser Ser Cys Asn  Gln Cys Asn Ala Glu  Ile Glu Pro
    1220                 1225                 1230

Gly Ser  Gly Phe Arg Cys Thr  Val Cys Pro Asp Phe  Asp Met Cys
    1235                 1240                 1245

Ala Ser  Cys Lys Val Asn Pro  His Lys Arg Ala Leu  Asp Glu Thr
    1250                 1255                 1260

Arg Gln  Arg Leu Thr Glu Ala  Glu Arg Arg Glu Arg  Asn Glu Gln
    1265                 1270                 1275

Leu Gln  Lys Thr Leu Ala Leu  Leu Val His Ala Cys  Gly Cys His
    1280                 1285                 1290

Asn Ser  Ala Cys Gly Ser Asn  Ser Cys Arg Lys Val  Lys Gln Leu
    1295                 1300                 1305

Phe Gln  His Ala Val His Cys  Gln Ser Lys Val Thr  Gly Gly Cys
    1310                 1315                 1320

Gln Leu  Cys Lys Lys Met Trp  Cys Leu Leu Asn Leu  His Ala Lys
    1325                 1330                 1335

Ser Cys  Thr Arg Ala Asp Cys  Pro Val Pro Arg Cys  Lys Glu Leu
    1340                 1345                 1350

Lys Glu  Leu Arg Arg Arg Gln  Thr Asn Arg Gln Glu  Glu Lys Arg
    1355                 1360                 1365

Arg Ala  Ala Tyr Ala Ala Met  Leu Arg Asn Gln Met  Ala Gly Ser
    1370                 1375                 1380

Gln Ala  Pro Arg Pro Met
    1385
```

<210> SEQ ID NO 3
<211> LENGTH: 1350
<212> TYPE: DNA
<213> ORGANISM: Artificial Sequence
<220> FEATURE:
<223> OTHER INFORMATION: LexA-p300 HAT Domain

<400> SEQUENCE: 3

```
atgaaggctc tcaccgctcg ccaacaggag gtctttgatc tgattcgcga ccacatctcg      60

cagaccggca tgccgccgac ccgggcggag attgctcagc ggctgggctt ccggagcccc     120

aacgcggccg aggagcacct gaaggccctc gcgcgcaagg gggtgatcga gattgtctcc     180

ggcgctagcc gcggcatccg cctgctgcag gaggaggagg agggcctgcc gctggtcggg     240
```

```
cgggtcgcgg ccggggagcc tctgctggcc cagcagcaca tcgagggcca ctaccaagtg    300
gacccctcgc tgtttaagcc caacgcggac ttcctgctcc gggtgtcggg catgagcatg    360
aaggacatcg gcatcatgga cggcgacctc ctggcggtgc acaagaccca ggacgtgcgc    420
aacggccagg tggtcgtcgc gcggattgac gacgaggtga ccgtgaagcg gctgaagaag    480
cagggcaaca aggtcgagct gctgcccgag aactcggagt tcaagcctat cgtggtcgac    540
ctgcgccagc agtccttcac catcgagggc ctggccgtgg gggtcatccg caacggtgac    600
tggctggagt tccccggcat ccggcgcccg tggcggccgc tggagtccac ctgcagccag    660
gcgaactccg gccgcatctc ctacgatctg gggtccttg aggtggccaa gccggagccg    720
ctgaccgtgc ggatgatcaa cagcgtgatg aagaagtgcg aggtcaagcc ccgcttccac    780
gagacgttcg gtccgaccga cggttacccc ggggagttcg gctaccggca gaaggtgctc    840
ctcctgttcc agtccctcga cggcgtcgac gtgtgcctgt tctgcatgta cgtgcaggag    900
tacgggaagg actgcccggc gcccaacacg aacgtggtgt acctgagcta cctggactcc    960
gtcaagtatt tccgccccga gattcccagc gccctgggcc ctgcggtgag cctgcggacc   1020
ttcgtgtacc accagctcct gattgcgtac gtggagttca cgcgcaacat gggcttcgag   1080
cagatgtaca tttggcgtg cccccccatg caggggggacg actatatcct gtattgccat   1140
cccacgaagc agaagacccc gcgctcggac cgcctgcgca tgtggtacat cgagatgctg   1200
aagctggcta aggaggaggg catcgtgaag cacctgtcga cgctgtggga cacctacttc   1260
gagggcggtc gcgaccaccg gatggagcgc tgcagcgtga cctacatccc ctacatggag   1320
ggcgactact ggcctggcga ggccgagtaa                                    1350
```

<210> SEQ ID NO 4
<211> LENGTH: 449
<212> TYPE: PRT
<213> ORGANISM: Artificial Sequence
<220> FEATURE:
<223> OTHER INFORMATION: LexA-p300 HAT Domain

<400> SEQUENCE: 4

```
Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Glu Gly Leu Pro Leu Val Gly
65                  70                  75                  80

Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
        115                 120                 125

Asp Leu Leu Ala Val His Lys Thr Gln Asp Val Arg Asn Gly Gln Val
    130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
```

```
                165                 170                 175

Ile Val Val Asp Leu Arg Gln Gln Ser Phe Thr Ile Glu Gly Leu Ala
            180                 185                 190

Val Gly Val Ile Arg Asn Gly Asp Trp Leu Glu Phe Pro Gly Ile Arg
        195                 200                 205

Arg Pro Trp Arg Pro Leu Glu Ser Thr Cys Ser Gln Ala Asn Ser Gly
    210                 215                 220

Arg Ile Ser Tyr Asp Leu Gly Val Leu Glu Val Ala Lys Pro Glu Pro
225                 230                 235                 240

Leu Thr Val Arg Met Ile Asn Ser Val Met Lys Lys Cys Glu Val Lys
                245                 250                 255

Pro Arg Phe His Glu Thr Phe Gly Pro Thr Asp Gly Tyr Pro Gly Glu
            260                 265                 270

Phe Gly Tyr Arg Gln Lys Val Leu Leu Leu Phe Gln Ser Leu Asp Gly
        275                 280                 285

Val Asp Val Cys Leu Phe Cys Met Tyr Val Gln Glu Tyr Gly Lys Asp
    290                 295                 300

Cys Pro Ala Pro Asn Thr Asn Val Val Tyr Leu Ser Tyr Leu Asp Ser
305                 310                 315                 320

Val Lys Tyr Phe Arg Pro Glu Ile Pro Ser Ala Leu Gly Pro Ala Val
                325                 330                 335

Ser Leu Arg Thr Phe Val Tyr His Gln Leu Leu Ile Ala Tyr Val Glu
            340                 345                 350

Phe Thr Arg Asn Met Gly Phe Glu Gln Met Tyr Ile Trp Ala Cys Pro
        355                 360                 365

Pro Met Gln Gly Asp Asp Tyr Ile Leu Tyr Cys His Pro Thr Lys Gln
    370                 375                 380

Lys Thr Pro Arg Ser Asp Arg Leu Arg Met Trp Tyr Ile Glu Met Leu
385                 390                 395                 400

Lys Leu Ala Lys Glu Glu Gly Ile Val Lys His Leu Ser Thr Leu Trp
                405                 410                 415

Asp Thr Tyr Phe Glu Gly Gly Arg Asp His Arg Met Glu Arg Cys Ser
            420                 425                 430

Val Thr Tyr Ile Pro Tyr Met Glu Gly Asp Tyr Trp Pro Gly Glu Ala
        435                 440                 445

Glu
```

<210> SEQ ID NO 5
<211> LENGTH: 720
<212> TYPE: DNA
<213> ORGANISM: Artificial Sequence
<220> FEATURE:
<223> OTHER INFORMATION: Codon Optimized Venus Gene Sequence

<400> SEQUENCE: 5

```
atggtgtcga agggtgagga gctgtttacc ggtgtcgtgc ctattctggt ggagctcgac      60

ggcgacgtca acgggcacaa gttttcggtg tccggcgagg gtgaggggga cgcgacgtac     120

ggcaagctca cgctgaagct gatctgcacc accggcaagc tgcccgtccc ctggccgacg     180

ctggtgacca ccctgggcta cggcctgcag tgcttcgccc gctacccgga ccacatgaag     240

cagcacgact tcttcaagtc ggccatgccc gaggggtacg tgcaggagcg cacgatcttc     300

tttaaggacg atggcaacta caagacccgc gctgaggtga agttcgaggg cgatacgctg     360

gtgaaccgca tcgagctcaa gggcatcgac ttcaaggagg acggcaacat cctgggtcac     420

aagctggagt acaactacaa ctcccacaac gtgtacatca cggcggataa gcagaagaac     480
```

ggcatcaagg ccaactttaa gattcgccat aacatcgagg acggcggcgt gcagctcgcc 540
gaccactacc agcagaacac cccgatcggc gacggccccg tgctgctgcc cgataaccac 600
tacctcagct accagtcggc cctgtccaag gatcccaacg agaagcgcga tcacatggtc 660
ctcctggagt tcgtgaccgc cgctggcatc accctgggca tggacgagct gtacaagtaa 720

<210> SEQ ID NO 6
<211> LENGTH: 239
<212> TYPE: PRT
<213> ORGANISM: Artificial Sequence
<220> FEATURE:
<223> OTHER INFORMATION: Codon Optimized Venus Sequence

<400> SEQUENCE: 6

Met Val Ser Lys Gly Glu Glu Leu Phe Thr Gly Val Val Pro Ile Leu
1 5 10 15

Val Glu Leu Asp Gly Asp Val Asn Gly His Lys Phe Ser Val Ser Gly
20 25 30

Glu Gly Glu Gly Asp Ala Thr Tyr Gly Lys Leu Thr Leu Lys Leu Ile
35 40 45

Cys Thr Thr Gly Lys Leu Pro Val Pro Trp Pro Thr Leu Val Thr Thr
50 55 60

Leu Gly Tyr Gly Leu Gln Cys Phe Ala Arg Tyr Pro Asp His Met Lys
65 70 75 80

Gln His Asp Phe Phe Lys Ser Ala Met Pro Glu Gly Tyr Val Gln Glu
85 90 95

Arg Thr Ile Phe Phe Lys Asp Asp Gly Asn Tyr Lys Thr Arg Ala Glu
100 105 110

Val Lys Phe Glu Gly Asp Thr Leu Val Asn Arg Ile Glu Leu Lys Gly
115 120 125

Ile Asp Phe Lys Glu Asp Gly Asn Ile Leu Gly His Lys Leu Glu Tyr
130 135 140

Asn Tyr Asn Ser His Asn Val Tyr Ile Thr Ala Asp Lys Gln Lys Asn
145 150 155 160

Gly Ile Lys Ala Asn Phe Lys Ile Arg His Asn Ile Glu Asp Gly Gly
165 170 175

Val Gln Leu Ala Asp His Tyr Gln Gln Asn Thr Pro Ile Gly Asp Gly
180 185 190

Pro Val Leu Leu Pro Asp Asn His Tyr Leu Ser Tyr Gln Ser Ala Leu
195 200 205

Ser Lys Asp Pro Asn Glu Lys Arg Asp His Met Val Leu Leu Glu Phe
210 215 220

Val Thr Ala Ala Gly Ile Thr Leu Gly Met Asp Glu Leu Tyr Lys
225 230 235

<210> SEQ ID NO 7
<211> LENGTH: 1428
<212> TYPE: DNA
<213> ORGANISM: Artificial Sequence
<220> FEATURE:
<223> OTHER INFORMATION: Venus-Bcl-x Fusion

<400> SEQUENCE: 7
atggtgtcga agggtgagga gctgtttacc ggtgtcgtgc ctattctggt ggagctcgac 60
ggcgacgtca acgggcacaa gttttcggtg tccggcgagg gtgaggggga cgcgacgtac 120
ggcaagctca cgctgaagct gatctgcacc accggcaagc tgcccgtccc ctggccgacg 180

```
ctggtgacca ccctgggcta cggcctgcag tgcttcgccc gctacccgga ccacatgaag    240

cagcacgact tcttcaagtc ggccatgccc gaggggtacg tgcaggagcg cacgatcttc    300

tttaaggacg atggcaacta caagacccgc gctgaggtga agttcgaggg cgatacgctg    360

gtgaaccgca tcgagctcaa gggcatcgac ttcaaggagg acggcaacat cctgggtcac    420

aagctggagt acaactacaa ctcccacaac gtgtacatca cggcggataa gcagaagaac    480

ggcatcaagg ccaactttaa gattcgccat aacatcgagg acggcggcgt gcagctcgcc    540

gaccactacc agcagaacac ccccgatcggc gacggccccg tgctgctgcc cgataaccac    600

tacctcagct accagtcggc cctgtccaag gatcccaacg agaagcgcga tcacatggtc    660

ctcctggagt tcgtgaccgc cgctggcatc accctgggca tggacgagct gtacaagggg    720

gtccttatga gccagagcaa ccgggagctg gtggtggact tcctgagcta caagctgagc    780

caaaagggct atagctggtc gcagttctcc gacgtcgagg agaaccggac cgaggccccc    840

gaggggaccg agtccgagat ggagacgccg agcgcgatta acggcaaccc gagctggcac    900

ctggcggact cccctgccgt gaacggcgcg accggccaca gctccagcct ggacgcgcgc    960

gaggtcatcc cgatggcggc cgtgaagcag gccctccgcg aggccggcga cgagttcgag   1020

ctgcgctatc gccgcgcttt ctcggacctg accagccagc tgcacatcac ccccggcacg   1080

gcttaccaaa gcttcgagca ggtggtgaac gagctgttcc gcgacggcgt gaactggggt   1140

cgcatcgtgg cgttcttcag cttcggcggt gcgctgtgcg tggagagcgt cgacaaggag   1200

atgcaggtgc tggtgtcgcg cattgcggct tggatggcca cctacctgaa cgaccacctg   1260

gagccctgga ttcaggagaa cggcggctgg gacaccttcg tcgagctgta cggcaacaac   1320

gctgcggcgg agagccgcaa gggccaagag cggttcaacc gctggttcct cacggggatg   1380

accgtggcgg gcgtcgtcct gctgggcagc ctgttctcgc ggaagtaa                1428
```

```
<210> SEQ ID NO 8
<211> LENGTH: 475
<212> TYPE: PRT
<213> ORGANISM: Artificial Sequence
<220> FEATURE:
<223> OTHER INFORMATION: Venus-Bclx Fusion

<400> SEQUENCE: 8

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Ile
        35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
```

```
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Gly
225                 230                 235                 240

Val Leu Met Ser Gln Ser Asn Arg Glu Leu Val Val Asp Phe Leu Ser
                245                 250                 255

Tyr Lys Leu Ser Gln Lys Gly Tyr Ser Trp Ser Gln Phe Ser Asp Val
            260                 265                 270

Glu Glu Asn Arg Thr Glu Ala Pro Glu Gly Thr Glu Ser Glu Met Glu
        275                 280                 285

Thr Pro Ser Ala Ile Asn Gly Asn Pro Ser Trp His Leu Ala Asp Ser
    290                 295                 300

Pro Ala Val Asn Gly Ala Thr Gly His Ser Ser Ser Leu Asp Ala Arg
305                 310                 315                 320

Glu Val Ile Pro Met Ala Ala Val Lys Gln Ala Leu Arg Glu Ala Gly
                325                 330                 335

Asp Glu Phe Glu Leu Arg Tyr Arg Arg Ala Phe Ser Asp Leu Thr Ser
            340                 345                 350

Gln Leu His Ile Thr Pro Gly Thr Ala Tyr Gln Ser Phe Glu Gln Val
        355                 360                 365

Val Asn Glu Leu Phe Arg Asp Gly Val Asn Trp Gly Arg Ile Val Ala
    370                 375                 380

Phe Phe Ser Phe Gly Gly Ala Leu Cys Val Glu Ser Val Asp Lys Glu
385                 390                 395                 400

Met Gln Val Leu Val Ser Arg Ile Ala Ala Trp Met Ala Thr Tyr Leu
                405                 410                 415

Asn Asp His Leu Glu Pro Trp Ile Gln Glu Asn Gly Gly Trp Asp Thr
            420                 425                 430

Phe Val Glu Leu Tyr Gly Asn Asn Ala Ala Ala Glu Ser Arg Lys Gly
        435                 440                 445

Gln Glu Arg Phe Asn Arg Trp Phe Leu Thr Gly Met Thr Val Ala Gly
    450                 455                 460

Val Val Leu Leu Gly Ser Leu Phe Ser Arg Lys
465                 470                 475
```

<210> SEQ ID NO 9
<211> LENGTH: 16
<212> TYPE: DNA
<213> ORGANISM: Artificial Sequence
<220> FEATURE:
<223> OTHER INFORMATION: LexA-Binding Site

<400> SEQUENCE: 9
ctgtatatat atacag 16

<210> SEQ ID NO 10
<211> LENGTH: 17
<212> TYPE: DNA
<213> ORGANISM: Artificial Sequence
<220> FEATURE:

-continued

```
<223> OTHER INFORMATION: DNA Binding Site for Gal4

<400> SEQUENCE: 10

cggaggacag tcctccg                                            17


<210> SEQ ID NO 11
<211> LENGTH: 230
<212> TYPE: PRT
<213> ORGANISM: Artificial Sequence
<220> FEATURE:
<223> OTHER INFORMATION: Protein ID:2293118 from NCBI Database

<400> SEQUENCE: 11

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Glu Gly Leu Pro Leu Val Gly
65                  70                  75                  80

Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
        115                 120                 125

Asp Leu Leu Ala Val His Lys Thr Gln Asp Val Arg Asn Gly Gln Val
    130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
            180                 185                 190

Val Gly Val Ile Arg Asn Gly Asp Trp Leu Glu Phe Pro Gly Ile Arg
        195                 200                 205

Arg Pro Trp Arg Pro Leu Glu Ser Thr Cys Ser Gln Ala Asn Ser Gly
    210                 215                 220

Arg Ile Ser Tyr Asp Leu
225                 230
```